United States Patent
Bowdish et al.

(10) Patent No.: US 6,803,230 B2
(45) Date of Patent: Oct. 12, 2004

(54) PHAGEMID VECTORS

(75) Inventors: Katherine S. Bowdish, Del Mar, CA (US); Shana Fredrickson, Solana Beach, CA (US); Martha Wild, Solana Beach, CA (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 12 days.

(21) Appl. No.: 10/134,188

(22) Filed: Apr. 26, 2002

(65) Prior Publication Data

US 2004/0175830 A1 Sep. 9, 2004

Related U.S. Application Data

(60) Provisional application No. 60/287,355, filed on Apr. 27, 2001.

(51) Int. Cl.[7] .................. C12N 15/63; C12N 15/64; C12N 15/65; C12N 15/70; C12N 15/73

(52) U.S. Cl. ................ 435/320.1; 435/69.1; 435/5; 536/23.1; 536/23.2; 536/23.4; 536/23.7; 536/24.1

(58) Field of Search .................... 435/320.1, 69.1, 435/5; 536/23.1, 23.2, 23.4, 23.7, 24.1

(56) References Cited

U.S. PATENT DOCUMENTS 5,658,727 A * 8/1997 Barbas et al. ................ 435/6

OTHER PUBLICATIONS

Krebber et al., Gene, 1996, vol. 178, pp. 71–74.*
"Genes", Benjamin Lewis, Ed., John Wiley & Sons, Inc., Chapter 13, "Termination and Antitermination", pp. 202–216.*

* cited by examiner

Primary Examiner—David Guzo

(57) ABSTRACT

Phagemid vectors containing a sequence of features between a Col E1 origin and an f1 origin are useful for display of polypeptides or proteins, including antibody libraries.

9 Claims, 46 Drawing Sheets

```
                                                                                          700
AGTGAGCTAACTCACATTAATTGGCGTTGCGCTCACTGCCCGCTTTCCAGTCGGGAAACCTGTCGTGCCAGCTGCATTAATGAATCGGCCAACGCGCGGGG
                      |—————————————|
                       CAP binding
                                                                                          800
AGAGGCGGTTTGCGTATTGGGCGCTCTTCCGCTTCCTCGCTCACTGACTCGCTGCGCTCGGTCGTTCGGCTGCGGCGAGCGGTATCAGCTCACTCAAAGG
 |——|                        |——|
  Tac                         Sap I
                                                                                          900
CGGTAATACGGTTATCCACAGAATCAGGGGATAACGCAGGAAAGAACATGTGAGCAAAAGGCCAGCAAAAGGCCAGGAACCGTAAAAAGGCCGCGTTGCT
                                                                                          1000
GGCGTTTTTCCATAGGCTCCGCCCCCCTGACGAGCATCACAAAAATCGACGCTCAAGTCAGAGGTGGCGAAACCCGACAGGACTATAAAGATACCAGGCG
                                                             |————————————————————————————|
                                                                        col E1
                                                                                          1100
TTTCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTC
|————————————————————————————————————————————————————————————————————————————————————————|
                                       col E1
                                                                                          1200
ATAGCTCACGCTGTAGGTATCTCAGTTCGGTGTAGGTCGTTCGCTCCAAGCTGGGCTGTGTGCACGAACCCCCCGTTCAGCCCGACCGCTGCGCCTTATC
|————————————————————————————————————————————————————————————————————————————————————————|
                                       col E1
```

*FIG. 4a (Cont.)*

```
ATCCAGTCTATTAATTGTTGCCGGGAAGCTAGAGTAAGTAGTTCGCCAGTTAATAGTTTGCGCAACGTTGTTGCCATTGCTACAGGCATCGTGGTGTCAC
                                                                                              2000
————————————————— beta lactamase —————————————————

GCTCGTCGTTTGGTATGGCTTCATTCAGCTCCGGTTCCCAACGATCAAGGCGAGTACATGATCCCCCATGTGTGCAAAAAAGCGGTTAGCTCCTTCGG
                                                                                              2100
————————————————— beta lactamase —————————————————

Pvu I
TCCTCCGATCGTTGTCAGAAGTAAGTTGGCCGCAGTGTATCACTCATGGTTATGGCAGCACYGCATAATTCTCTTACTGTCATGCCATCCGTAAGATGC
                                                                                              2200
————————————————— beta lactamase —————————————————

TTTTCTGTGACTGGTGAGTACTCAACCAAGTCATTCTGAGAATAGTGTATGCGGCGACCGAGTTGCTCTTGCCCGGCGTCAATACGGGATAATACCGCGC
                                                                                              2300
————————————————— beta lactamase —————————————————

CACATAGCAGAACTTTAAAAGTGCTCATCATTGGAAAACGTTCTTCGGGGCGAAAACTCTCAAGGATCTTACCGCTGTTGAGATCCAGTTCGATGTAACC
                                                                                              2400
————————————————— beta lactamase —————————————————

CACTCGTGCACCCAACTGATCTTCAGCATCTTTTACTTTCACCAGCGTTTCTGGGTGAGCAAAAACAGGAAGGCAAAATGCCGCAAAAAAGGGAATAAGG
                                                                                              2500
————————————————— beta lactamase —————————————————
```

*FIG. 4b (Cont.)*

GCGACACGGAAATGTTGAATACTCATACTCTTCCTTTTTCAATATTATTGAAGCATTTATCAGGGTTATTGTCTCATGAGCGGATACATATTTGAATGTA 2600

— beta lactamase —

TTTAGAAAAATAAACAAATAGGGGTTCCGCGCACATTTCCCCGAAAAGTGCCAC 2654

*FIG. 4c*

```
GCTCCAAGCTGGGCTGTGTGCACGAACCCCCGTTCAGCCCGGACCGCTGCGCCCTTATCCGGTAACTATCGTCTTGAGTCGTCCAACCCGGTAAGACACGACTT    1300
                                     |____col E1____|

ATCGCCACTGGCAGCAGCCACTGGTAACAGGATTAGCAGAGCGGAGTATGTAGGCGGTGCTACAGAGTTCTTGAAGTGGTGGCCTAACTACGGCTACACT        1400
                                     |____col E1____|

AGAAGGACACAGTATTTGGTATCTGCGCTCTCTGCTGAAGCCAGTTACCTTCGGGAAAAAGAGTTGGTAGCTCTTGATCCGGCAAACAAACCACCGCTGGTAGCG  1500
                                     |____col E1____|

GTGGTTTTTTGTTTGCAAGCAGCAGATTACGGCGCAGAAAAAAAGGATCTCAAGAAGATCCTTTGATCTTTTCTACGGGGTCTGACGCTCAGTGGAACGA        1600
                                     |___col E1___|

AAACTCACGTTAAGGGATTTTGGTCATGAGATTATCAAAAAGGATCTTCACCTAGATCCTTTTAAATTAAAAATGAAGTTTTAAATCAATCTAAAGTATA        1700

TATGAGTAAACTTGGTCTGACAGTTACCAATGCTTAATCAGTGAGGCACCTATCTCAGCGATCTGTCTATTTCGTTCATCCATAGTTGCCTGACTCCCCG       1800
```

FIG. 6b

```
TCGTGTAGATAACTACGATACGGGAGGGCTTACCATCTGGCCCCAGTGCTGCAATGATACCGCGAGACCCACGCTCACCGGCTCCAGATTTATCAGCAAT   1900

AAACCAGCCAGCGGCGGGAAGGGCCGAGCGCAGAAGTGGTCCTGCAACTTTATCCGCCTCCATCCAGTCTATTAATTGTTGCCGGGAAGCTAGAGTAAGTAGT   2000

TCGCCAGTTAATAGTTTGCGCAACGTTGTTGCCATTGCTACAGGCATCGTGGTGTCACGCTCGTCGTTTGGTATGGCTTCATTCAGCTCCGGTTCCCAAC   2100

Pvu I
GATCAAGGCGAGTTACATGATTCCCCCATGTTGTGCAAAAAAGCGGTTAGCTCCTTCGGTCCTCCGATCGTTGTCAGAAGTAAGTTGGCCGCAGTGTTATC   2200

ACTCATGGTTATGGCAGCACTGCATAATTCTCTTACTGTCATGCCATCCGTAAGATGCTTTTCTGTGACTGGTGAGTACTCAACCAAGTCATTCTGAGAA   2300

TAGTGTATGCGGCGACCGAGTTGCTCTTGCCCGGCGTCAATACGGGATAATACCGCGCCACATAGCAGAACTTTAAAAGTGCTCATCATTGGAAAACGTT   2400

CTTCGGGGCGAAAACTCTCAAGGATCTTACCGCTGTTGAGATCCAGTTCGATGTAACCCACTCGTGCACCCAACTGATCTTCAGCATCTTTTACTTTCAC   2500
```

*FIG. 6b (Cont.)*

CAGCGTTTCTGGGTGAGCAAAAACAGGAAGGCAAAATGCCGCAAAAAAGGGAATAAGGGCGACACGGAAATGTTGAATACTCATACTCTTCCTTTTCAA 2600

TATTATTGAAGCATTTATCAGGGTTATTGTCTCATGAGCGGATACATATTTGAATGTATTTAGAAAAAATAAACAAATAGGGGTTCCGGCGCACATTTCCCC 2700

GAAAAGTGCCAC 2712

FIG. 6c (Seq. ID No. 21)

GTGGCACTTTTCGGGGAAATGTGCGCGGAACCCCTATTTGTTTATTTTTCTAAATACATTCAAATATGTATCCGCTCATGAGACAATAACCCTGATAAAT  100

GCTTCAATAATATTGAAAAAGGAAGAGTATGAGTATTCAACATTTCCGTGTCGCCCTTATTCCCTTTTTTGCGGCATTTTGCCTTCCTGTTTTTGCTCAC  200
                                     ———————————— beta lactamase ————————————

CCAGAAACGCTGGTGAAAGTAAAAGATGCTGAAGATCAGTTGGGTGCACGAGTGGGTTACATCGAACTGGATCTCAACAGCGGTAAGATCCTTGAGAGTT  300
———————————————————————————————————————— beta lactamase ————————————————————————————————————————————

TTCGCCCCGAAGAACGTTTTCCAATGATGAGCACTTTTAAAGTTCTGCTATGTGGCGCGGTATTATCCCGTATTGACGCCGGGCAAGAGCAACTCGGTCG  400
———————————————————————————————————————— beta lactamase ————————————————————————————————————————————

CCGCATACACTATTCTCAGAATGACTTGGTTGAGTACTCACCAGTCACAGAAAAGCATCTTACGGATGGCATGACAGTAAGAGAATTATGCAGTGCTGCC  500
———————————————————————————————————————— beta lactamase ————————————————————————————————————————————
                                                              Pvu I ATAACCATGAGTGATAACACTGCGGCCAACTTACTTCTGACAACGATCGGAGGACCGAAGGAGCTAACCGCTTTTTTGCACAACATGGGGGATCATGTAA  600
———————————————————————————————————————— beta lactamase ————————————————————————————————————————————

*FIG. 8a*

```
CTCGCCTTGATCGTTGGGAACCGGAGCTGAATGAAGCCATACCAAACGACGAGCGTGACACCACGATGCCTGTAGCAATGGCAACAACGTTGGCGCAAACT  700
                   ————— beta lactamase —————

ATTAACTGGCGAACTACTTACTCTAGCTTCCCGGCAACAATTAATAGACTGGAGGCGGATAAAGTTGCAGGACCACTTCTGCGCTCGGCCCTTCCG  800
                   ————— beta lactamase —————

GCTGGCTGGTTTATTGCTGATAAATCTGGAGCCGGTGAGCGTGGGTCTCGCGGTATCATTGCAGCACTGGGGCCAGATGGTAAGCCCTCCCGTATCGTAG  900
                   ————— beta lactamase —————

TTATCTACACGACGGGGAGTCAGGCAACTATGGATGAACGAAATAGACAGATCGCTGAGATAGGTGCCTCACTGATTAAGCATTGGTAACTGTCAGACCA  1000
                   ————— beta lactamase —————

AGTTTACTCATATATACTTTAGATTGATTTAAAACTTCATTTTTAATTTAAAAGGATCTAGGTGAAGATCCTTTTTGATAATCTCATGACCAAAATCCCT  1100

TAACGTGAGTTTTCGTTCCACTGAGCGTCAGACCCCGTAGAAAAGATCAAAGGATCTTCTTGAGATCCTTTTTTTCTGCGCGTAATCTGCTGCTTGCAAA  1200
                                                                              ←——————— col E1

CAAAAAAACCACCGCTACCAGCGGTGGTTTGTTTGCCGGATCAAGAGCTACCAACTCTTTTTCCGAAGGTAACTGGCTTCAGCAGAGCGCAGATACCAAA  1300
————— col E1
```

FIG. 8a (Cont.)

```
TACTGTCCTTCTAGTGTAGGCCGTAGTTAGGCCACCACTTCAAGAACTTGTAGCACCGCCTACATACCTGCCTCTGCTAATCCTGTTACCAGTGGCTGCT
                                                                                                    1400
                            |————— col E1 ——————|

GCCAGTGGCGATAAGTCTGTGTCTTACCGGGTTGGACTCAAGACGATAGTTACCGGATAAGGCGCAGCGGTCGGGCTGAACGGGGGGTTCGTGCACACAGC
                                                                                                    1500
                              |————— col E1 ——————|

CCAGCTTGGAGCGAACGACCTACACCGAACTGAGATACCTACAGCGTGAGCTATGAGAAAGCGCCACGCTTCCCGAAGGGAGAAAAGGCGGACAGGTATCC
                                                                                                    1600
                                |————— col E1 ——————|

GGTAAGCGGCAGGGTCGGAACAGGAGAGCGCACGAGGGAGCTTCCAGGGGGGAAACGCCTGGTATCTTTATAGTCCTGTGTCGGGTTTCGCCACCTCTGACTT
                                                                                                    1700
                              |————— col E1 ——————|

GAGCCGTCGATTTTTGTGATGCTCGTCAGGGGGGCGGAGCCTATGAGAAAAACGCCAGCAACGCGGCCCTTTTACGGTTCCTGGCCTTTTGCTGGCCTTTTG
                                                                                                    1800
        |——— col E1 ———|

CTCACATGTTCTTTCCTGCGTTATCCCTGATTCTGTGGATAACCGTATTACCGCCTTTGAGTGAGCTGATACCGCTCGCCGCAGCCGAACGACCGAGCG
                                                                                                    1900

CAGCGAGTCAGTGAGCGAGGAAGCGGTACCCGATAAAAGGGCTTCCTGACAGGAGGCCGTTTTGTTTTGCAGCCCACCTAGGGAAGAGCGCCCAATACG
                                                                                                    2000
        |— Term linker —|                                                        |⋮|              |— lac —|
         ■— Tr Term —■                                                           Sap I FIG. 8b
```

```
CAAAACCGCCTCTCCCCGCGCGTTGGCCGATTCATTAATGCAGCTGGCACGACAGGTTTCCCGACTGGAAAGCGGGCAGTGAGCGCAACGCAATTAATGTG    2100
                                                    |_____|
                                                                           lac EcoR I   Xba I
AGTTAGCTCACTCATTAGGCACCCCAGGCTTTACACTTTATGCTTCCGGCTCGTATGTTGTGTGGAATTGTGAGCGGATAACAATTGAATTCACATCTAG    2200
|_____|                                                                                  |___|
       lac                                                                                         rep Xho I        Spe I        Sfi I    Not I              Pvu I
ATATCTCGAGTCAATAACTACTAGTGGGCCAGGCCGGCCATTACCGATCGCCTTCCCAACAGTTGCGCAGCCTGAATGGCGAATGGGACGCGCCC         2300
                                                                                          |_____
                                                                                             f1 origin TGTAGCGGCGCATTAAGCGCGGCGGGTGTGGTGGTTACGCGCAGCGTGACCGCTACACTTGCCAGCGCCCTAGCGCCCGCTCCTTTCGCTTTCTTCCCTT    2400
_____
                                         f1 origin CCTTTCTCGCCACGTTCGCCGGCTTTCCCCGTCAAGCTCTAAATCGGGGGCTCCCTTTAGGGTTCCGATTTAGTGCTTTACGGCACCTCGACCCCAAAAA    2500
_____
                                         f1 origin ACTTGATTAGGGTGATGGTTCACGTAGTGGGCCATCGCCCTGATAGACGGTTTTTCGCCCTTTGACGTTGGAGTCCACGTTCTTTAATAGTGGACTCTTG    2600
_____
                                         f1 origin TTCCAAACTGGAACAACACTCAACCCTATCTCGGTCTATTCTTTTGATTTATAAGGGATTTTGCCGATTTCGGCCTATTGGTTAAAAAATGAGCTGATTT    2700
_____
                                         f1 origin
```

*FIG. 8b (Cont.)*

Seq. ID No. 18

```
GTGGCACTTTTCGGGGAAATGTGCGCGGAACCCCTATTTGTTATTTTCTAAATACATTCAAATATGTATCCGCTCATGAGACAATAACCCTGATAAAT    100
                 Ear I
GCTTCAATAATATTGAAAAAGGAAGAGTATGAGTATTCAACATTTCCGTGTCGCCCTTATTCCCTTTTTGCGGCATTTTGCCTTCCTGTTTTTGCTCAC    200
                                           ———————————————— beta lactamase
CCAGAAACGCTGGTGAAAGTAAAAGATGCTGAAGATCAGTTGGGTGCACGAGTGGGTTACATCGAACTGGATCTCAACAGCGGTAAGATCCTTGAGAGTT    300
————————————————————————————————————————— beta lactamase
TTCGCCCCGAAGAACGTTTTCCAATGATGAGCACTTTTAAAGTTCTGCTATGTGGCGCGGTATTATCCCGTATTGACGCCGGGCAAGAGCAACTCGGTCG    400
————————————————————————————————————————— beta lactamase
CCGCATACACTATTCTCAGAATGACTTGGTTGAGTACTCACCAGTCACAGAAAAGCATCTTACGGATGGCATGACAGTAAGAGAATTATGCAGTGCTGCC    500
————————————————————————————————————————— beta lactamase
ATAACCATGAGTGATAACACTGCGGCCAACTTACTTCTGACAACGATCGGAGGACCGAAGGAGCTAACCGCTTTTTTGCACAACATGGGGATCATGTAA    600
————————————————————————————————————————— beta lactamase
```

*FIG. 11a*

```
CTCGGCCTTGATCGTTGGGAACCGGAGCTGAATGAAGCCATACCAAACGACGAGCGTGACACCACGATGCCTGTAGCAATGGCAACAACGTTGCGCAAACT   700
                        —————————————————————————— beta lactamase ——————————————————————————

ATTAACTGGCGAACTACTTACTCTAGCTTCCCGGCAACAATTAATAGACTGGATGGAGGCGGATAAAGTTGCAGGACCACTTCTGCGCTCGGCCCTTCCG   800
                        —————————————————————————— beta lactamase ——————————————————————————

GCTGGCTGGTTTATTGCTGATAAATCTGGAGCCGGTGAGCGTGGGTCTCGCGGTATCATTGCAGCACTGGGGCCAGATGGTAAGCCCTCCCGTATCGTAG   900
                        —————————————————————————— beta lactamase ——————————————————————————

TTATCTACACGACGGGGGAGTCAGGCAACTATGGATGAACGAAATAGACAGATCGCTGAGATAGGTGCCTCACTGATTAAGCATTGGTAACTGTCAGACCA  1000
                        —————————————————————————— beta lactamase ——————————————————————————

AGTTTACTCATATATACTTTAGATTGATTTAAAACTTCATTTTTAATTTAAAAGGATCTAGGTGAAGATCCTTTTTGATAATCTCATGACCAAAATCCCT  1100

TAACGTGAGTTTTCGTTCCACTGAGCGTCAGACCCCGTAGAAAAGATCAAAGGATCTCTTGAGATCCTTTTTTTCTGCGCGTAATCTGCTGCTTGCAAA  1200
                                                                                            ←—— col E1

CAAAAAAACCACCGCTACCAGCGGTGGTTTGTTTGCCGGATCAAGAGCTACCAACTCTTTTTCCGAAGGTAACTGGCTTCAGCAGAGCGCAGATACCAAA  1300
—————————————————————————————————————— col E1 ——————————————————————————————————————
```

*FIG. 11a (Cont.)*

```
TACTGTCCTTCTAGTGTAGCCGTAGTTAGGCCACCACTTCAAGAACTCTGTAGGCCACCGCCTACATACCTCGCTCTGCTAATCCTGTTACCAGTGGCTGCT    1400
                                    col E1

GCCAGTGGCGATAAGTCGTGTCTTACCGGGTTGGACTCAAGACGATAGTTACCGGATAAGGCGCAGCGGTCGGGCTGAACGGGGGGTTCGTGCACACAGC    1500
                                col E1

CCAGCTTGGAGCGGAACGACCTACACCGAACTGAGATACCTACAGCGTGAGCTATGAGAAAGCGCCACGCTTCCCGAAGGGAGAAAGGCGGACAGGTATCC    1600
                              col E1

GGTAAGGCGCAGGGTCGGAACAGAGAGCGCACGAGGGAGCTTCCAGGGGGAAACGCCAGCAACGCGGCCTATGGAAAAACGCCAGCAACGCGGCCTTTTTATAGTCCTGTCGGGTTTCGCCACCTCTGACTT    1700
                                      col E1

GAGCGTCGATTTTTGTGATGCTCGTCAGGGGGGCGGAGCCGGAGCCTATGGAAATAACGCCAGCAACGCGGCCTTTTACGGTTCCTGGCCTTTTGCTGGCCTTTTG    1800
                col E1

CTCACACATGTTCTTTCTGCGTTATCCCCTGATTCTGTGGATAACCGTATTACCGCCTTTGAGTGAGCTGATACCGCTCGCCGCAGCCGAACGACCGAGCG    1900
                                                                                          Ear I
                                                                                          Sap I

CAGGCGAGTCAGTGAGCGAGGAAGCGGAAGAGCGTACCCGATAAAAGCGGGCTTCCTGACAGGAGGCCGTTTTTGTTTTTGCAGCCCACCTAGCGGAAGAGCGCCCAATACG    2000
                    Term linker                                                                      lac
                 ─── Tr Term ───
```

*FIG. 11b*

```
AGGGCTGTCTGTGGAATGCTACAGGCGTTGTAGTTTGTACTGGTGACGAAACTCAGTGTTACGGTACATGGGTTCCTATTGGGCTTGCTATCCCTGAAAA
                                                                                                  2600
——————————————————— f1 gIII ———————————————————

TGAGGGTGGCGGTTCTGAGGGTGGCGGTTCTGAGGGTGGCGGTTCTGAGGGTGGCGGTACTAAACCTCCTGAGTACGGTGATACACCTATTCCGGGCTAT
                                                                                                  2700
——————————————————— f1 gIII ———————————————————

ACTTATATCAACCCTCTCGACGGCACTTATCCGCCTGGTACTGAGCAAAACCCCGCTAATCCTAATCCTTCTCTTGAGGAGTCTCAGCCTCTTAATACTT
                                                                                                  2800
——————————————————— f1 gIII ———————————————————

TCATGTTTCAGAATAATAGGTTCCGAAATAGGCAGGGGCATTAACTGTTTATACGGGCACTGTTACTCAAGGCACTGACCCCGTTAAAACTTATTACCA
                                                                                                  2900
——————————————————— f1 gIII ———————————————————

GTACACTCCTGTATCATCAAAAGGCCATGTATGACGCTTACTGGAACGGTAAATTCAGAGACTGCGCTTTCCATTCTGGCTTTAATGAGGATCCATTCGTT
                                                                                                  3000
——————————————————— f1 gIII ———————————————————

TGTGAATATCAAGGCCAATCGTCTGACCTGCCTCAACCTCCTGTTAATGCTGGCGGCGGCTCTGGTGGTGGTTCTGGTGGCGGCTCTGAGGGTGGTGGCT
                                                                                                  3100
——————————————————— f1 gIII ———————————————————

CTGAGGGTGGCGGTTCTGAGGGTGGCGGCTCTGAGGGTGGCGGTTCCGGTGGCGGCTCCGGTTCCGGTGATTTTGATTATGAAAAGATGGCAAACGCTAA
                                                                                                  3200
——————————————————— f1 gIII ———————————————————
```

```
CTCGGCCACGTTCGCCGGCTTTCCCCGTCAAGCTCTAAATCGGGGGCTCCCTTTAGGGTTCCGATTTAGTGCTTTACGGCACCTGACCCCAAAAAACTTG 3900
                              f1 ori ATTAGGGTGATGGTTCACGTAGTGGGCCATGCCCCTTTGACGTTGGAGTCCACGTTCTTTAATAGTGGACTCTTGTCCA 4000
                              f1 ori AACTGGAACAACACTCAACCCTATCTCGGTCTATTCTTTTGATTTATAAGGGATTTTGCCGATTTCGGCCTATTGGTTAAAAAATGAGCTGATTTAACAA 4100
                              f1 ori AAATTTTAACGCGGAATTTTAACAAAATATTAACGCTTACAATTTAG 4145
         f1 ori
```

FIG. 11d (SEQ. ID NO. 25)
XbaI
---CTCGAGCTGATGAGCCATGGAAGCTGTGTCGCCTGCACCAGGCTCCCACGGCTCGTGGTGCGGTGCGCTTCTGGTGTTCGCTGCCTACAGCCGACACGTC  100
━━━━━━━━ stuffer ━━━━━━━━

GAGCTTCGTGCCCCTAGAGTTGGCGCGTCACAGCAGCCTCCGGGCGCTCCGGATATCACCGTGTCATCCACATCAATGAAGTAGTGCTCTAGACGCCCCC  200
━━━━━━━━ stuffer ━━━━━━━━

GTGGGGCTGGTGGCGCGGTTGGCTGACGAGAGCGGCCACGTAGTGTTGCCCTGGCTCCCGCCGCCTGAGACACCCATGACGTCTCACATCCGCTACGAGG  300
━━━━━━━━ stuffer ━━━━━━━━

TGGACGTCTCCGGCCGCAACGCGCAGGGAGCGTACAGAGGGTGGAGATCTGGAGGGCCGCACCGAGTGTGCTGAGCAACCTGCGGGGCCGGACGCG  400
━━━━━━━━ stuffer ━━━━━━━━

CTACACCCTTCGCCGTCCGCGCGTATGGCTGAGCGCAGCTTCGGCGGCTTCTGGAGCGCCTGGTCGGAGCCTGTGTCGCTGCTGACGCCTAGCGACCTG  500
━━━━━━━━ stuffer ━━━━━━━━

GACCCCCTCATCCTGACGCTCTCCCCTCATCCTCGTTGGTCATCCTGGTGCTGCATCCGGTGCTGACCGTGCTGCTCTCCCACGCCGGGCTCTGAAGCAGAAGA  600
━━━━━━━━ stuffer ━━━━━━━━

TCTGGGCCTGGCATCCCGAGCCCAGAGCCCAGAGAGCGAGTTTGAAGGCCCTCTTCACCACCCACAAGGGTAACTTCCAGCTGTGGCTGTACCAGAATGATGGCTGCCT  700
━━━━━━━━ stuffer ━━━━━━━━

FIG. 12B (SEQ. ID NO. 29)
XhoI
CTCGAGCTGATGAGCCATGGAAGCTGTGTCGCCTGCACCAGGCTCCCACGGCTGTGGTGCGGTGCGCTTCTGGTGTTCGCTGCCTACAGCCGACACGTC 100 stuffer

GAGCTTCGTGCCCTAGAGAGTTGCGCGTCACAGCAGCCTCCGGCGCTCCGGCGATATCACCGTGTCATCCACATCAAGTAGTGCTCCTAGACGCCCCC 200 stuffer

GTGGGGCTGGTGGCGCGGTTGGCTGACGAGAGCGGGCCACGTAGTGTTGCGCTGGCTCCCCGCGCCTGAGACACCCATGACGTCTCACATCCGCTACGAGG 300 stuffer

TGGACGTCTCGGCCGGCAACGGCGCAGGGAGGAGCGTACAGAGAGGGTGGAGATCCTGGAGGGCCGCACCGAGTGTGCTGAGCAACCTGCGGGGCCGGACGCG 400 stuffer

CTACACCTTCGCCGTCCCGCGCGTATGGCTGAGCCGAGCTTCGGCGGCTTCTGGAGGCGCCTGTGTCGCTGCTGACGCCTAGCGCACCTG 500 stuffer

GACCCCCTCATCTCGACGCTCTCCCTCATCCTGGTCATCCTGGTGCTGCTGACCGTGCTGCGGCTGCTCTCCCACCGCCGGGCTCTGAAGCAGAAGA 600 stuffer

TCTGGCCTGGCATCCCGAGCCCAGAGAGCGAGTTTGAAGGCCTCTTCACCACCACCAAAGGGTAACTTCCAGCTGTGGCTGTACCAGAATGATGGCTGCCT 700 stuffer

FIG. 12F (SEQ. ID NO. 30)
XhoI
CTCGAGCTGATGAGCCATGGAAGCTGTGTCGCCTGCACCAGGCTCGTGGTGCGGTGCGCTTCTGGTGTTCGCTGCTACAGCCGACACGTC  100
----stuffer----

GAGCTTCGTGCCCCTAGAGTTGCGCGTCACAGCAGCCTTCCCGGCGCTCCCGGATATCACCGTGTCATCCACATCAATGAAGTAGTGCTCCTAGACGCCCCC  200
----stuffer----

GTGGGGCTGGTGCGCGGGTTTGGCTGACGAGAGCGGGCCACGTAGTGTTGCGCTGGCCTCCCGCCGCCTGAGACACCCATGACGTCTCACATCCGCTACGAGG  300
----stuffer----

TGGACGTCTCGGCCGGCCAACGGGCGCAGGGAGCGTACAGAGGGTGGAGATCCTGGAGGGCCACCGAGTGTGTGCTGAGCAACCTGCGGGGCCGGACGCG  400
----stuffer----

CTACACCTTCGCGCCGTCCGCGCGCGTATGGCTGAGCCGAGCTTCGGCGGCTCTGGAGGCCTGTGTCGCTGTGACGCCTAGCGACCTG  500
----stuffer----

GACCCCCTCATCCTGACGCTCTCCCTCATCCTCGTGGTCATCCTGGTCGCTGACCGTGCTGCGGCGTCCTCCCACCGCCGGGCTCTGAAGCAGAAGA  600
----stuffer----

TCTGGGCCTGGCATCCCGAGCCTCTTCACCACCACAAGGGTAACTTCCAGCTGTGGCTGTACCAGAATGATGGCTGCCT  700
----stuffer----

FIG. 12G (SEQ. ID NO. 31)

GTGGCACTTTTCGGGGAAATGTGCGCGGAAACCCCTATTTGTTTATTTTTCTAAATACATTCAAATATGTATCCGCTCATGAGACAATAACCCTGATAAAT 100

GCTTCAATAATATTGAAAAAGGAAGAGTATGAGTATTCAACATTTCCGTGTCGCCCTTATTCCCTTTTTTGCGGCATTTTGCCTTCCTGTTTTTGCTCAC 200
　　　　　　　　　　　　　　　　　　　　　　　　　　　　　　|————— beta lactamase CCAGAAACGCTGGTGAAAGTAAAAGATGCTGAAGATCAGTTGGGTGCACGAGTGGGTTACATGCGAACTGGATCTCAACAGCGGTAAGATCCTTGAGAGTT 300
　　　　　　　　　　　　　　　　　　　　　　　　beta lactamase —————|

TTCGCCCCGAAGAACGTTTTCCAATGATGAGCACTTTTAAAGTTCTGCTATGTGGCGCGGTATTATCCCGTATTGACGCCGGGCAAGAGCAACTCGGTCG 400
|————— beta lactamase CCGCATACACTATTCTCAGAATGACTTGGTTGAGTACTCACCAGTCACAGAGAAAAGCATCTTACGGATGGCATGACAGTAAGAGAATTATGCAGTGCTGCC 500
　　　　　beta lactamase —————|

ATAACCATGAGTGATAACACTGCGGCCAACTTACTTCTGACAACGATCGGAGGACCGAAGGAGCTAACCGCTTTTTTGCACAACATGGGGGATCATGTAA 600
|————— beta lactamase CTCGCCTTGATCGTTGGGAACCGGAGCTGAATGAAGCCATACCAAAGACGAGCTGACACCACGATGCCTGTAGCAATGGCAACAACGTTGCGCAAACT 700
　　　　　　beta lactamase

FIG. 13A

ATTAACTGGGGAACTACTTACTCTAGCTTCCCGGCAACAATTAATAGACTGGAGTGAGGCGGATAAAGTTGCAGGACCACTTCTGCGCTCGGCCCTTCCG 800
              beta lactamase GCTGGCTGGTTTATTGCTGATAAATCTGGAGCCGGTGAGCGTGGGTCTCGCGGTATCATTGCAGCACTGGGGCCAGATGGTAAGCCCTCCGTATCGTAG 900
              beta lactamase TTATCTACACGACGGGGAGTCAGGCAACTATGGATGAACGAAATAGACAGATCGCTGAGATAGGTGCCTCACTGATTAAGCATTGGTAACTGTCAGACCA 1000
              beta lactamase AGTTTACTCATATATACTTTAGATTGATTTAAAACTTCATTTTTAATTTAAAAGGATCTAGGTGAAGATCCTTTTTGATAATCTCATGACCAAAATCCCT 1100

TAACGTGAGTTTTCGTTCCACTGAGCGTCAGACCCCGTAGAAAAGATCAAAGGATCTTCTTGAGATCCTTTTTTTCTGCGCGTAATCTGCTGCTTGCAAA 1200
                                                                              col E1

CAAAAAAACCACCGCTACCAGCGGTGGTTTGTTTGCCGGATCAAGAGCTACCAACTCTTTTTCCGAAGGTAACTGGCTTCAGCAGAGCGCAGATACCAAA 1300
col E1

TACTGTCCTTCTAGTGTAGCCGTAGTTAGGCCACCACTTCAAGAACTCTGTAGCACCGCCTACATACCTCGCTCTGCTAATCCTGTTACCAGTGGCTGCT 1400
col E1

GCCAGTGGCGATAAGTCGTGTCTTACCGGGTTGGACTCAAGACGATAGTTACCGGATAAGGCGCAGCGGTCGGGCTGAACGGGGGGTTCGTGCACACAGC 1500
col E1

```
TAATACTTTCATGTTTCAGAATATAGGTTCCGAAATAGGCAGGGGCATTAACTGTTTATACGGGCACTGTTACTCAAGGCACTGACCCGTTAAAACT    2900
                                          f1 gIII

TATTACCAGTACACTCCTGTATCATCAAAAGCCATGTATGACGCTTACTGGAACGGTAAATTCAGAGACTGCGCTTTCCATTCTGGCTTTAATGAGGATC 3000
                                          f1 gIII

CATTCGTTTGTGAATATCAAGGCCAATCGTCTGACCTGCCTCAACCTCCTGTTAATGCTGGCGGCGCTCTGGTGGTGGTTCTGGTGGCGGCTCTGCGGG  3100
                                          f1 gIII

TGGTGGCTCTGAGGGTGGCGGTTCTGAGGGTGGCGGCTCTGAGGGTGGCGGGTTCCGGTTGGTCCTCGGTGATTTTGATTATGAAAAGATGGCA       3200
                                          f1 gIII

AACGCTAATAAGGGGGCTATGACCGAAAATGCCGATGAAAACGCGCTACAGTCTGACGCTAAAGGCAAACTTGATTCTGTCGCTACTGATTACCGTGCTG 3300
                                          f1 gIII

CTATCGACGGTTTCATTGGTGACGTTTCCGGCCTTGCTAATGGTAATGGTGCTACTGGTGATTTTGCTGGCTCTAATTCCCAAATGGCTCAAGTCGGTGA 3400
                                          f1 gIII

CGGTGATAATTCACCTTTAATGAATAATTTCCGTCAATATTTACCTTCCCTCCCTCAATCGGTTGAATGTCGCCCTTTTGTCTTTGGCGCTGGTAAACCA 3500
                                          f1 gIII

TATGAATTTTCTATTGATTGTGACAAAATAAACTTATTCCGTGGTGTCTTTGCGTTTCTTTTATATGTTGCCACCTTTATGTATGTATTTTCGACGTTTG 3600
                                          f1 gIII
```

FIG. 13C

PHAGEMID VECTORS

This application claims priority under 35 USC 119(e) to provisional application 60/287,355, filed Apr. 27, 2001.

BACKGROUND

1. Technical Field

This disclosure relates to cloning vectors. More specifically, phagemid vectors useful in the cloning and expression of foreign genetic information are disclosed.

2. Background of Related Art

Plasmids are extrachromosomal genetic elements capable of autonomous replication within their hosts. Bacterial plasmids range in size from 1 Kb to 200 Kb or more and encode a variety of useful properties. Plasmid encoded traits include resistance to antibiotics, production of antibiotics, degradation of complex organic molecules, production of bacteriocins, such as colicins, production of enterotoxins, and production of DNA restriction and modification enzymes.

Although plasmids have been studied for a number of years in their own right, particularly in terms of their replication, transmissibility, structure and evolution, with the advent of genetic engineering technology the focus of plasmid research has turned to the use of plasmids as vectors for the cloning and expression of foreign genetic information. In its application as a vector, the plasmid should possess one or more of the following properties. The plasmid DNA should be relatively small but capable of having relatively large amounts of foreign DNA incorporated into it. The size of the DNA insert is of concern in vectors based on bacteriophages where packing the nucleic acid into the phage particles can determine an upper limit. The plasmid should be under relaxed replication control. That is, where the replication of the plasmid molecule is not strictly coupled to the replication of the host DNA (stringent control), thereby resulting in multiple copies of plasmid DNA per host cell. The plasmid should express one or more selectable markers, such as the drug resistance markers, mentioned above, to permit the identification of host cells which contain the plasmid and also to provide a positive selection pressure for the maintenance of the plasmid in the host cell. Finally the plasmid should contain a single restriction site for one or more endonucleases in a region of plasmid which is not essential for plasmid replication. A vector as described above is useful, for example, for cloning genetic information, by which is meant integrating a segment of foreign DNA into the vector and reproducing identical copies of that information by virtue of the replication of the plasmid DNA.

The next step in the evolution of vector technology was the construction of so-called expression vectors. These vectors are characterized by their ability not only to replicate the inserted foreign genetic information but also to promote the transcription of the genetic information into mRNA and its subsequent translation into protein. This expression requires a variety of regulatory genetic sequences including but not necessarily limited to promoters, operators, transcription terminators, ribosomal binding sites and protein synthesis initiation and termination codons. These expression elements can be provided with the foreign DNA segment as parts thereof or can be integrated within the vector in a region adjacent to a restriction site so that when a foreign DNA segment is introduced into the vector it falls under the control of those elements to which it is now chemically joined.

Filamentous bacteriophage consist of a circular, single-stranded DNA molecule surrounded by a cylinder of coat proteins. There are about 2,700 molecules of the major coat proteins pVIII that envelope the phage. At one end of the phage particle, there are approximately five copies of each of gene III and VI proteins (pIII and pVI) that are involved in host cell binding and in the termination of the assembly process. The other end contains five copies of each of pVII and pIX that are required for the initiation of assembly and for maintenance of virion stability. In recent years, vectors have been developed and utilized for the display of foreign peptides and proteins on the surface of filamentous phage or phagemid particles.

The display of peptides and proteins on the surface of phage or phagemid particles represents a powerful methodology for selection of rare members in a complex library and for carrying out molecular evolution in the laboratory. The ability to construct libraries of enormous molecular diversity and to select for molecules with predetermined properties has made this technology applicable to a wide range of problems. A few of the many applications of such technology are: i) phage display of natural peptides including, mapping epitopes of monoclonal and polyclonal antibodies and generating immunogens; ii) phage display of random peptides, including mapping epitopes of monoclonal and polyclonal antibodies, identifying peptide ligands, and mapping substrate sites for proteases and kinases; and iii) phage display of protein and protein domains, including directed evolution of proteins, isolation of antibodies and cDNA expression screening.

Vectors have been developed which incorporate DNA from plasmids and bacteriophage. These phagemid vectors are derived by modifications of a plasmid genome containing an origin of replication from a bacteriophage, (e.g. f1, M13, fd) as well as the plasmid origin of replication. Phagemids are useful for the expression of foreign genetic information.

One known phagemid vector is pBluescript II KS+ (pBS II KS+) (Stratagene, La Jolla, Calif.), which is a useful starting point for the construction of the present vector because of its small size and the fact that it contains the colE1 plasmid origin of replication and the phage f1 origin of replication in the desired orientation. The plasmid also carries an ampicillin resistance gene.

Vectors which due to their structures provide enhanced functionality would be desirable.

SUMMARY

Novel plasmid vectors capable of replication and expression of foreign genetic information in bacteria, such as, for example, cyanobacterium and *E. coli* are described herein. These new vectors contain a specific sequence of features after the ColE1 origin but before the f1 origin. Specifically, the present phagemid vector contains, after the ColE1 origin but before the f1 origin, a bacterial transcription terminator, a promoter, a first ribosomal binding site, a first leader sequence and a first cloning region, a second ribosomal binding site, a second leader sequence and a second cloning region. The second cloning region is adapted to receive a gene encoding a polypeptide to be displayed and a nucleotide sequence encoding at least a functional domain of a display protein.

The vectors described herein are constructed through a series of steps which convert a starting vector through a series of intermediate plasmids to the present novel vector which can be used for display of antibody libraries.

BRIEF DESCRIPTION OF THE DRAWINGS

FIGS. 4A–C show the sequence (Seq. ID No. 19) of intermediate vector p110-81.6;

FIGS. 6A–C show the sequence (Seq. ID No. 20) of intermediate vector p131-03.7;

FIGS. 8A–C show the sequence (Seq. ID No. 21) of intermediate vector p131-39.1;

FIGS. 11A–D show the nucleic acid sequence (Seq. ID No. 18) of plasmid pAX131, including the domains corresponding to particular genes.

FIGS. 13A–C show the nucleic acid sequence of plasmid pAX131 Xba/Not.

DETAILED DESCRIPTION OF PREFERRED EMBODIMENTS

Figure 1:
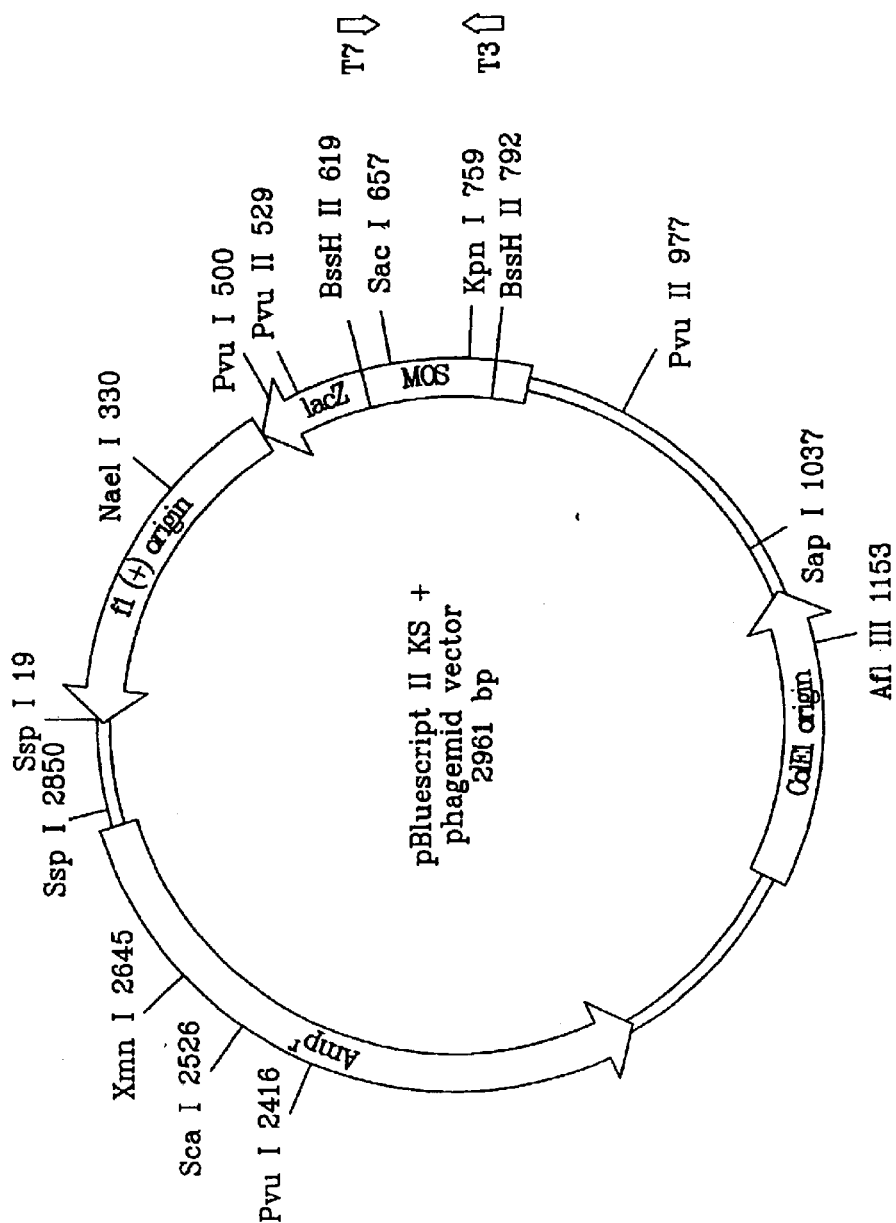
FIG. 1 schematically illustrates the structure of pBS II KS+, a useful starting vector for making the novel vectors described herein.

The present novel phagemid vectors are useful for display of polypeptides such as, for example, antibody libraries. The vectors described herein can be prepared using any commercially available vector containing a ColE1 and an f1 origin of replication as the starting material. Such starting materials are known and are commercially available. One suitable starting material is the vector pBS II KS+ which is commercially available from Stratagene Corp., La Jolla, Calif. (See FIG. 1).

Figure 2:
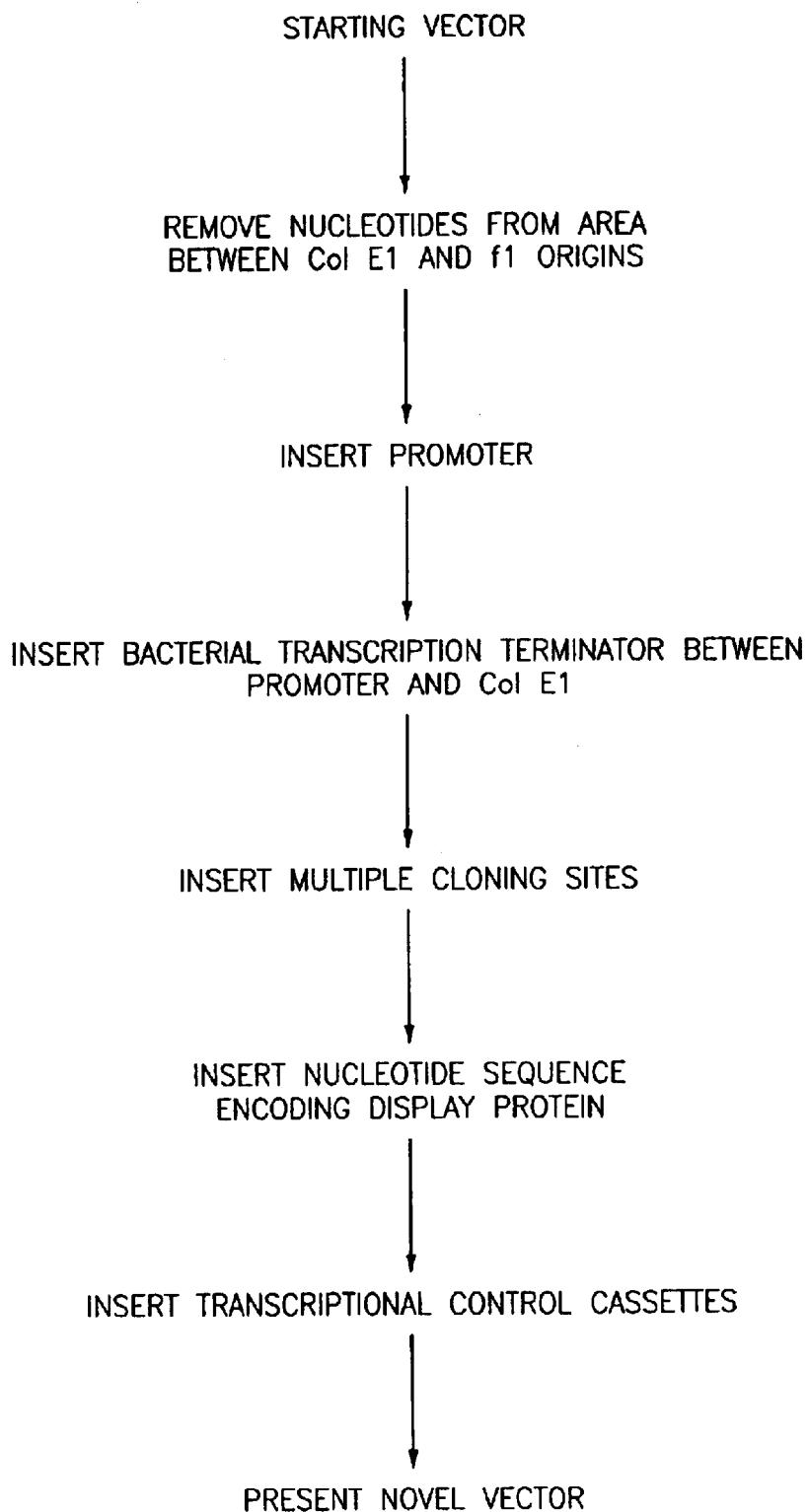
FIG. 2 is a flow chart illustrating the method of making the novel vectors described herein.

FIG. 2 is a flow-chart showing one embodiment of the steps involved in converting a starting vector into one of the present novel vectors. Those skilled in the art will readily envision other schemes for preparing the present vectors. Accordingly, the present disclosure is not limited to the sequence of steps shown in FIG. 2.

In the first step, the starting vector is digested with restriction enzymes to remove a substantial portion of the vector between the ColE1 origin and the f1 origin of replication. Typically, the portion to be removed from the starting vector includes multiple cloning sites. Depending on the particular restriction sites present in the starting vector, suitable methods for digesting the starting vector are known to and readily selected by those skilled in the art.

Next, a promoter is inserted downstream of the ColE1 origin of the digested starting vector. Any promoter recognized by a host cell can be employed. Suitable promoters include, but are not limited to, ara, lac and trc promoters. The promoter drives expression of other sequences inserted into the vector, such as, for example expression of polypeptides. In particularly useful embodiments, a promoter sequence generated from the starting vector is employed as the promoter inserted downstream of the ColE1 origin as described in more detail below.

In the next step, a bacterial transcription terminator is inserted downstream of the ColE1 origin, and upstream of the promoter. Any terminator recognized by a host cell can be employed. Suitable terminators include, but are not limited to, the $t_{HP}$ terminator, the bgIG terminator, and the crp terminator. It should be noted that bioinformatics analysis has allowed the identification of over 100 rho-independent transcription terminators in the E. coli genome, all of which should be suitable for this purpose (Ermolaeva, et al, J. Mol Biol 301:27–33 (2000)).

In the next step, multiple restriction sites are inserted downstream of the promoter. The restriction site can be any known restriction site. Suitable restriction sites for insertion include, but are not limited to Nhe I, Hind III, Nco I, Xma I, Bgl II, Bst I, Pvu I, etc. The number of restriction sites inserted is not critical, provided a sufficient number of restriction sites are inserted to allow completion of the balance of the steps needed to create the present novel vectors. Thus as few as 2 to as many as 10 or more restriction sites can be inserted in this step. It should be understood that if one or more of the restriction sites selected for insertion is present in the starting vector, it may be desirable to remove or disable the native restriction site to avoid unwanted digestion during further processing. The restriction site can be inserted using any technique known to those skilled in the art. A particularly preferred combination of restriction sites inserted in this step is Not I, Sfi I, Spe I, Xho I, Xba I and EcoR I.

The next step involves inserting a nucleotide sequence encoding a product that enables display of a polypeptide on the surface of a phagemid particle. The product encoded can thus be considered at least a functional domain of a display protein. The display protein can be any natural or synthetic polypeptide to which a polypeptide to be displayed can be fused and which can present the polypeptide to be displayed for screening processes. Suitable display polypeptides include proteins that can be incorporated into the coat of a phage particle. As those skilled in the art will appreciate, filamentous bacteriophage consist of a circular, single-stranded DNA molecule a surrounded by a cylinder of coat proteins. There are about 2,700 molecules of the major coat protein pVIII that encapsidate the phage. At one end of the phage particle, there are approximately five copies each of gene III and VI proteins (pIII and pVI) that are involved in host-cell binding and in the termination of the assembly process. The other end contains five copies each of pVII and pIX that are required for the initiation of assembly and for maintenance of virion stability. A nucleotide sequence encoding any of these coat proteins can be employed in making the novel vectors herein. Particularly preferred are nucleotide sequences encoding at least a functional domain of pIII. The nucleotide sequence encoding at least a functional domain of pIII can be natural or synthetic. The nucleotide sequence inserted can encode a truncated pIII provided the display function of the protein is maintained. An example of a synthetic or artificial coat protein useful herein is that disclosed in Weiss et al., J. Mol. Biol., 300(1), 213–219 (2000), the disclosure of which is incorporated herein by reference.

In the next step, two transcriptional control cassettes are inserted, an upstream transcriptional control cassette and a downstream transcriptional control cassette. Each of the transcriptional control cassettes include a ribosomal binding site, a leader sequence and a cloning site for receiving a gene encoding a polypeptide to be expressed. Any known ribosomal binding site (RBS) and leader sequence recognized by the host cell can be employed. Preferably, the RBS and leader sequence employed is optimized for expression in *E. coli*. The cloning site is a region of the nucleic acid between two restriction sites, typically with a nonessential region of nucleotide sequence (commonly referred to as a "stuffer" sequence) positioned therebetween. Alternatively, the stuffer sequence may contain a non-essential region and a portion of an antibody constant domain. Suitable stuffer sequences include, for example, those shown in FIGS. 12A–G.

The downstream transcriptional control cassette is inserted adjacent to the nucleotide sequence encoding at least the functional domain of the display protein. In this manner, a fusion protein will be expressed when a gene encoding a polypeptide to be displayed is inserted at the cloning site of the downstream transcriptional control cassette. As those skilled in the art will appreciate, a suppressible stop codon could be positioned between the gene encoding the polypeptide to be displayed and the nucleotide sequence encoding at least a functional domain of the display protein such that fusion display is obtained in a suppressing host (as long as the gene is inserted in-frame) and a secreted protein without the display protein is obtained in a non-suppressing host.

The upstream transcriptional control cassette is inserted upstream of the downstream transcriptional control cassette. The upstream transcriptional control cassette provides a second cloning region for receiving a second gene encoding a polypeptide that can dimerize with the polypeptide to be displayed. For example, where the vector expresses a heavy chain Fd fused to a display protein, the second gene preferably encodes an antibody light chain. As with the cloning site of the downstream transcriptional control cassette, the cloning site of the upstream transcriptional control cassette is a region of the vector between two restriction sites, typically with a stuffer positioned therebetween. It should of course be understood that where a polypeptide other than an antibody is to be displayed (such as, for example, where monomeric display of a single polypeptide or protein is intended) a second gene need not be cloned into the vector at the cloning site of the upstream transcriptional control cassette. In such cases the second cloning site can simply remain unused. As those skilled in the art will also appreciate, where a single chain antibody is encoded by the gene inserted at the cloning site of the downstream transcriptional control cassette, there is no need to insert a second gene into the vector at the cloning site of the upstream transcriptional control cassette.

Thus, the phagmid vector produced by the process illustrated in FIG. 2 will contain, after the ColE1 origin but before the f1 origin, a terminator, a promoter, a first ribosomal binding site, a first leader sequence and a first cloning region, a second ribosomal binding site, a second leader sequence and, a second cloning region for receiving a gene encoding a polypeptide to be displayed and a nucleotide sequence encoding at least a functional domain of a display protein.

The present vectors also include a selectable marker. Either an ampicillin resistant or a CAT resistant vector can be produced in accordance with the present disclosure. The ampicillin or CAT resistance can be provided by simply choosing a starting vector having the desired resistance. Alternatively, if the starting vector is ampicillin resistant to produce a CAT resistant vector, the ampicillin resistant gene is removed and replaced with the chloramphenicol transferase gene. Techniques for providing either ampicillin or CAT resistance in the present vectors will be readily apparent to those skilled in the art. Other suitable selectable markers include, but are not limited to, tetracycline or kanamycin resistance.

The vectors described herein can be transformed into a host cell using known techniques (e.g., electroporation) and amplified. The vectors described herein can also be digested and have a first gene and optionally a second gene ligated therein in accordance with this disclosure. The vector so engineered can be transformed into a host cell using known techniques and amplified or to effect expression of polypeptides and/or proteins encoded thereby to produce phage particles displaying single polypeptides or dimeric species. Those skilled in the art will readily envision other uses for the novel vectors described herein.

The following examples illustrate the present invention without limiting its scope. The steps involved in constructing the vectors described herein are discussed in detail in the Examples. Those skilled in the art possess knowledge of suitable techniques to accomplish the steps described below without the need for undue experimentation, such techniques being well known to those skilled in the art.

EXAMPLE 1

This example illustrates methods and compositions for the construction of one embodiment of a phagemid vector according to the present disclosure. The starting phagemid selected for construction was pBS II KS+ which contains an ampicillin resistant gene which results in a final vector, pAX131, which is ampicillin resistant.

Digestion of Starting Vector and Insertion of Promoter

Figure 3:
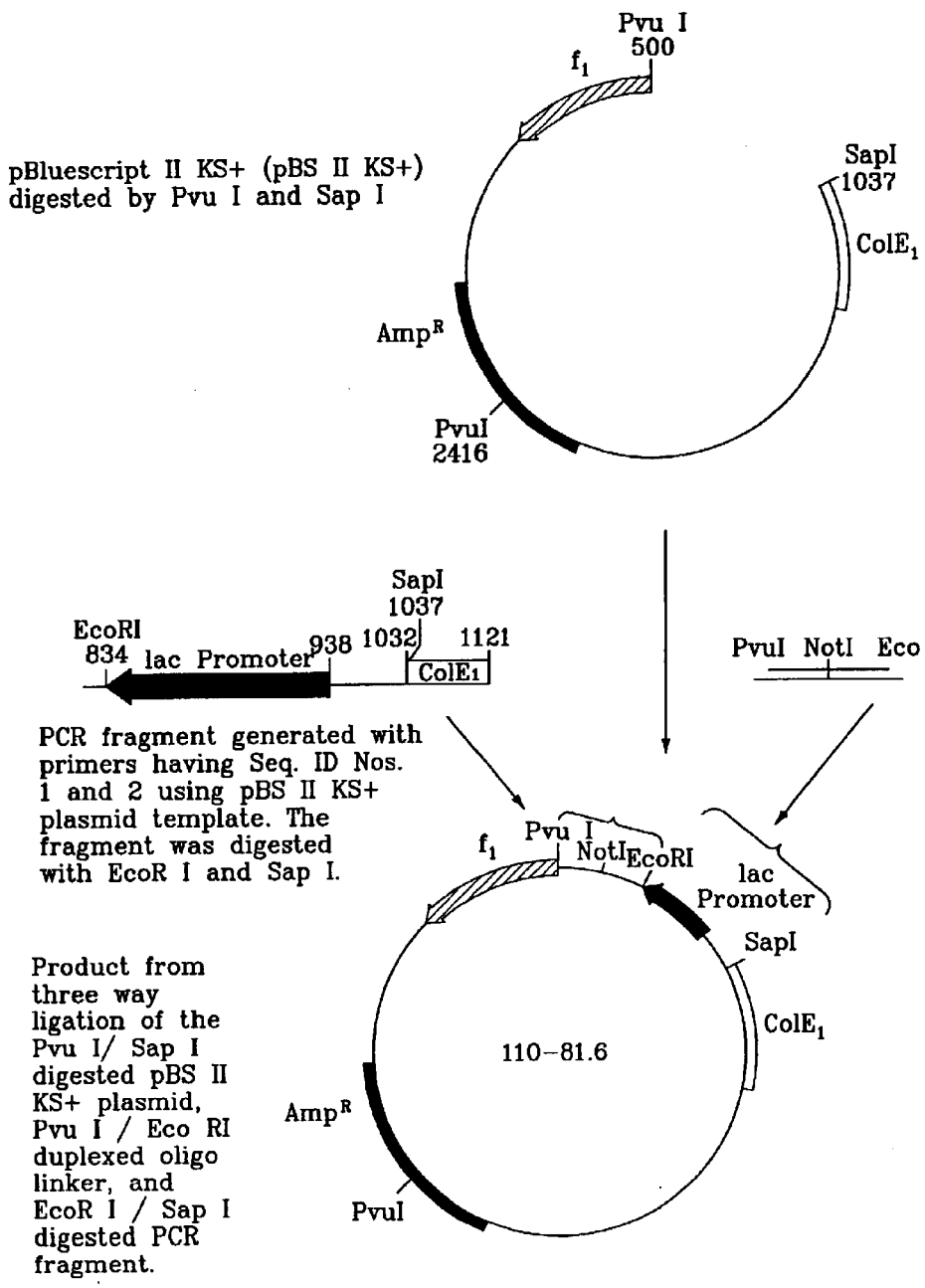
FIG. 3 schematically illustrates the digestion of the starting vector and insertion of the promoter.

The commercially available vector pBS II KS+ (Stratagene, LaJolla, Calif.) was digested with Pvu I and Sap I to generate a 2424 bp pBS II KS+ fragment which lacks the bases at positions 500 to 1037 corresponding to the multiple cloning region. The resulting fragment contains the Ampicillin resistant gene (AmpR), phage f1 origin, and the Col E1origin. (See FIG. 3.) Next, two mutagenic primers were used with the pBS II KS+ fragment in a PCR reaction followed by digestion with EcoR I and Sap I to generate a 209 bp fragment containing the lac promoter. The primers used were as follows:

5' AAC CGT ATT ACC GCC TTT GAG TG 3' (SEQ. ID. NO. 1);

and

5' CCT GAA TTC AAT TGT TAT CCG CTC ACA ATT CCA C 3' (SEQ. ID. NO. 2).

The 2424 bp fragment and the 209 bp fragment were combined in a three-way ligation reaction with two overlapping oligonucleotides which contain a Not I, EcoR I and Pvu I sites to form a first intermediate plasmid (designated p110-81.6). (See FIG. 3.) The oligonucleotides used for this reaction were:

5' CGG TAA TGC GGC CGC TAC ATG 3' (SEQ. ID. NO. 3);

and

5' AAT TCA TGT AGC GGC CGC ATT ACC GAT 3' (SEQ. ID. NO. 4).

Figure 4A:
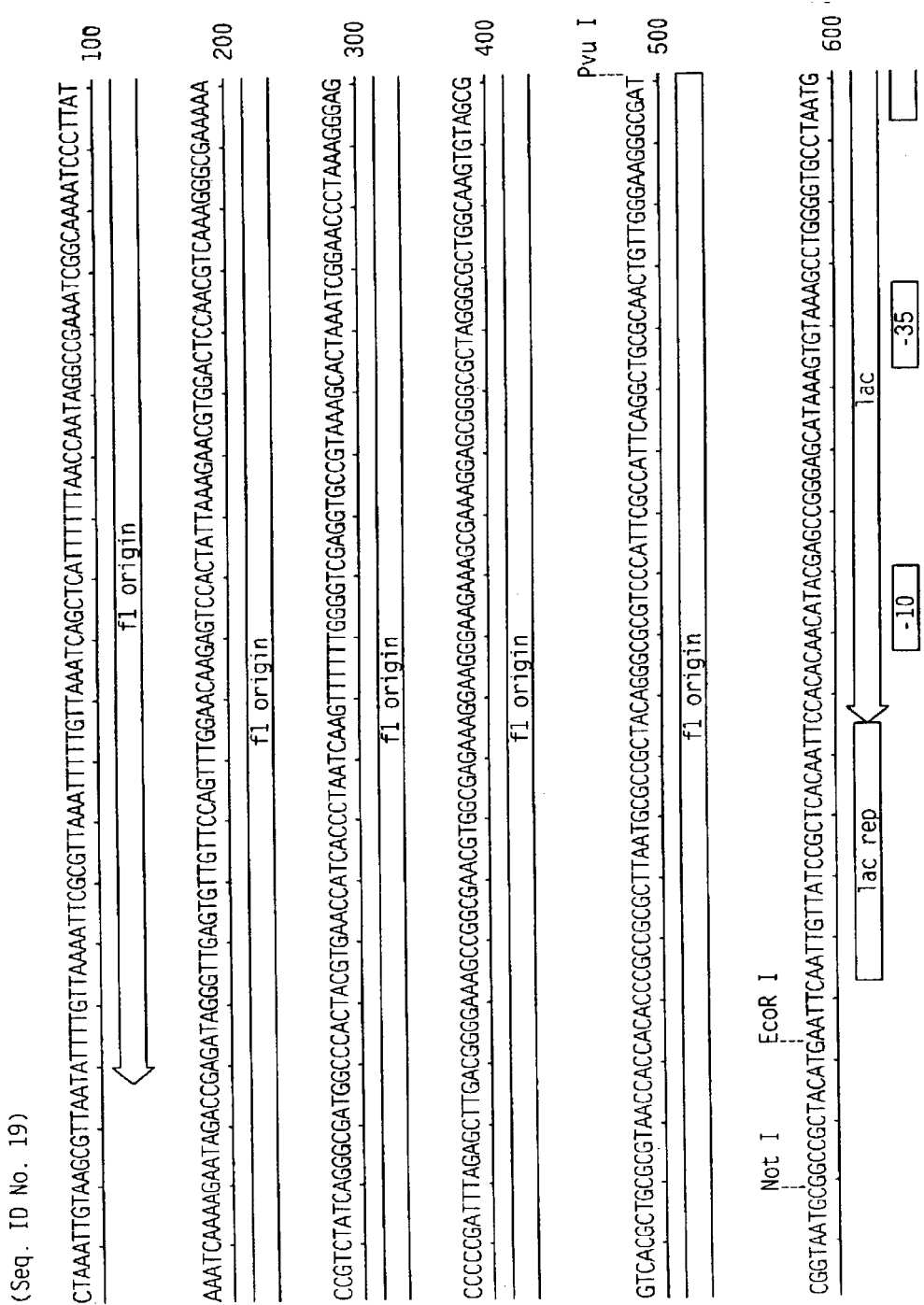
Figure 4B:

The resulting plasmid p110-81.6 was digested and sequenced in the altered region to identify a clone with the correct incorporation of the lac promoter, Pvu I, Sap I, EcoR, and Not I sites. The sequencing of p110-81.6 revealed a nucleic acid change at position 875 within the lac promoter. The published sequence of pBS II KS+ had an adenine at position 875. However, sequencing of p110-81.6 and the original pBS II KS+ revealed a guanine at position 875. The sequence (Seq. ID No. 19) of intermediate plasmid p110-81.6 is shown in FIGS. 4A–C.

Insertion of Terminator

Figure 5:
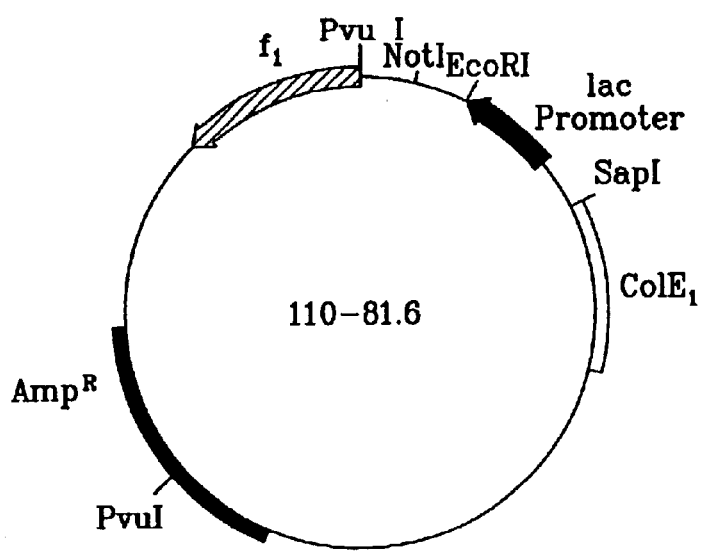
FIG. 5 schematically illustrates the insertion of the terminator.
Figure 5:
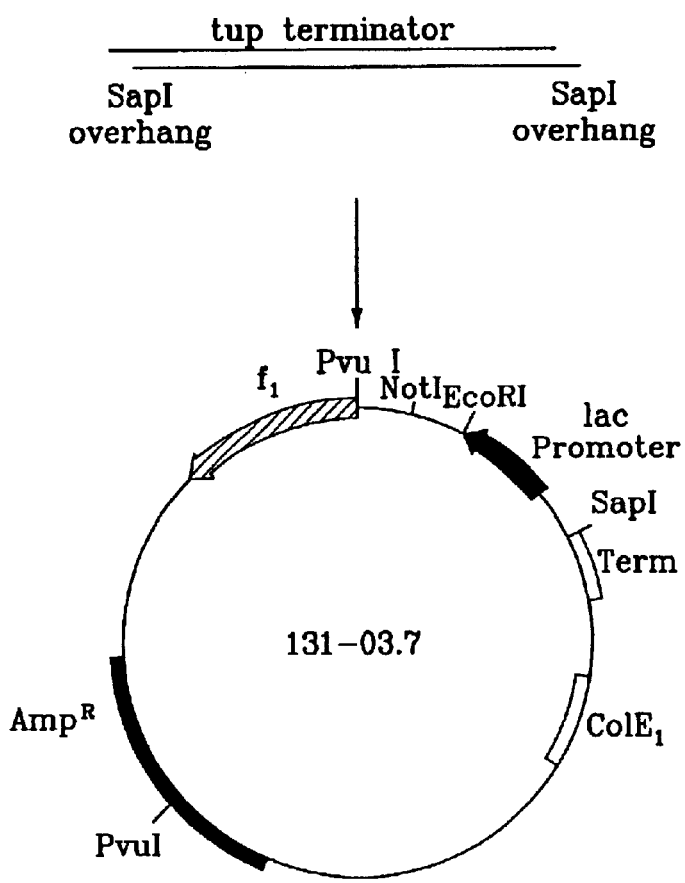

A transcription termination sequence was inserted into the first intermediate plasmid (p110-81.6) upstream of the lac promoter at the Sap I site. (See FIG. 5.)

Plasmid 110-81.6 was digested with Sap I to create an insertion point for the oligonucleotides which contained a $t_{HP}$ terminator (Nohno et al., Molecular and General Genetics, Vol. 205, pages 260–269 (1986). The oligonucleotides used in this ligation were:

> 5' AGC GTA CCC GAT AAA AGC GGC TTC CTG ACA GGA GGC CGT TTT GTT TTG CAG CCC ACC T 3'; (SEQ. ID. No. 5);

and

> 5' GCT AGG TGG GCT GCA AAA CAA AAC GGC CTC CTG TCA GGA AGC CGC TTT TAT CGG GTA C 3' (SEQ. ID. NO. 6).

Figure 6A:
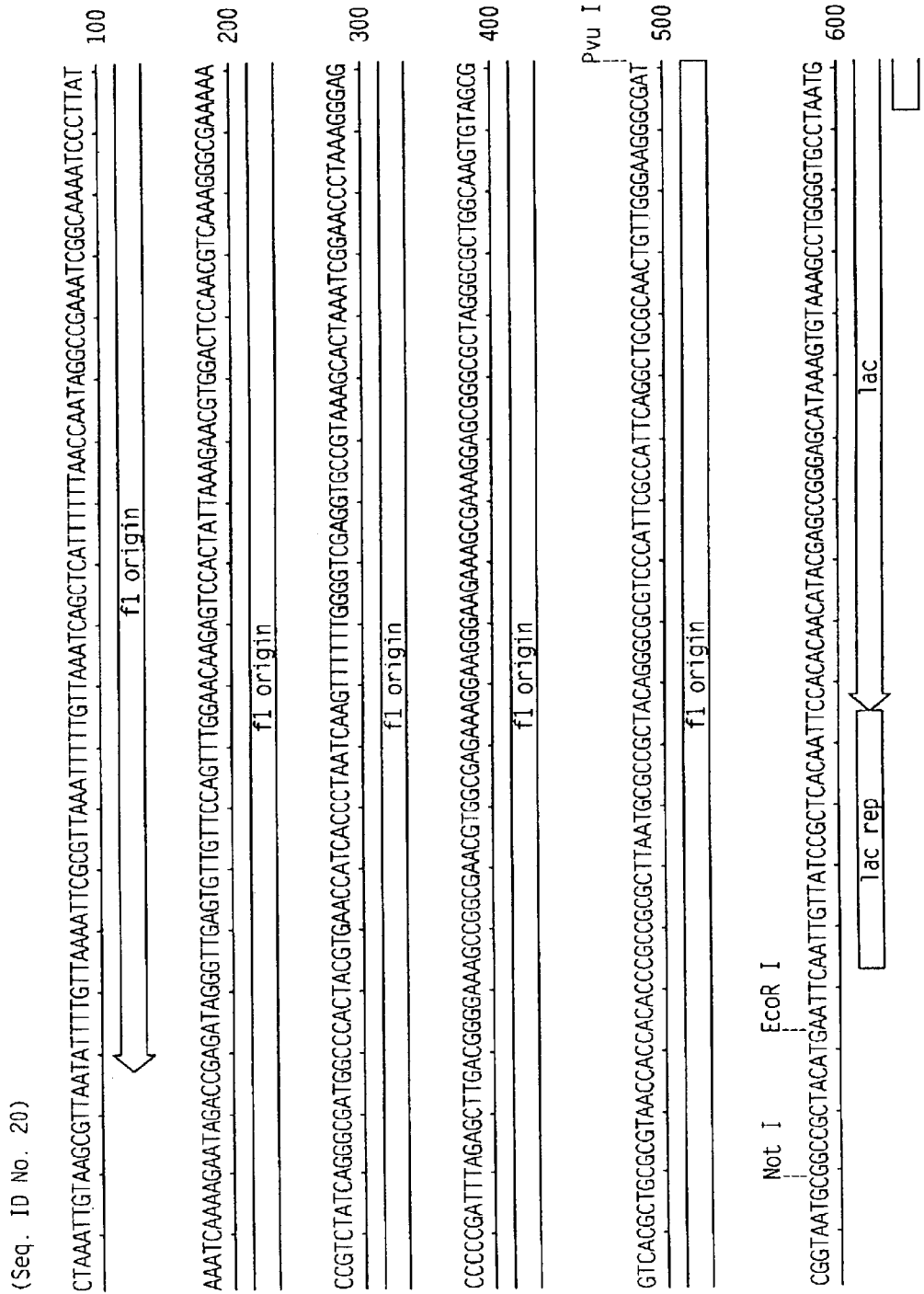
Figure 6A:
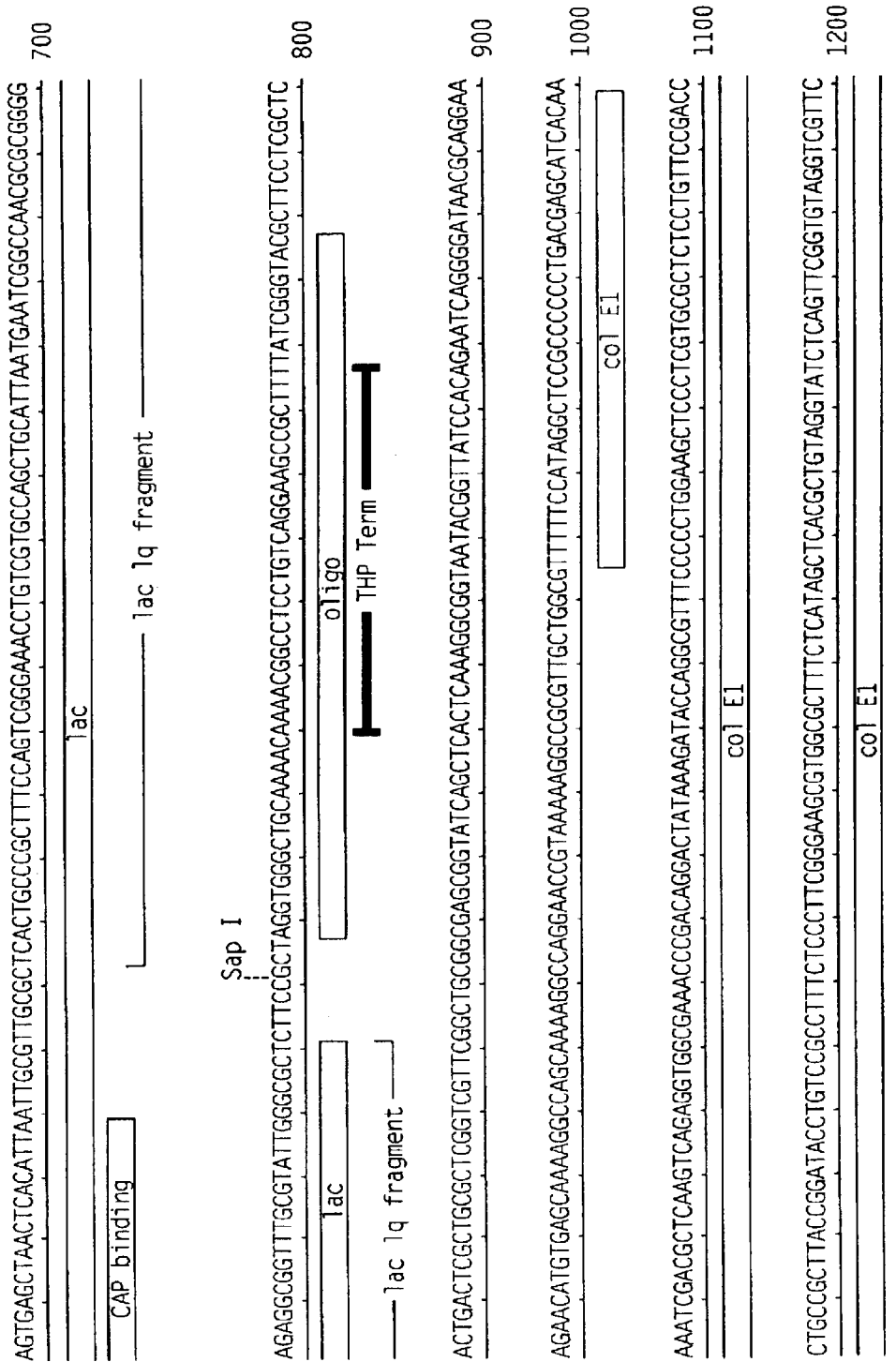

The resulting intermediate vector (designated p131-03.7) was digested and sequenced in the altered region to determine its identity. The sequence (Seq. ID No. 20) of intermediate vector p131-03.7 is shown in FIGS. 6A–C.

Insertion of Multiple Restriction Sites

Figure 7:
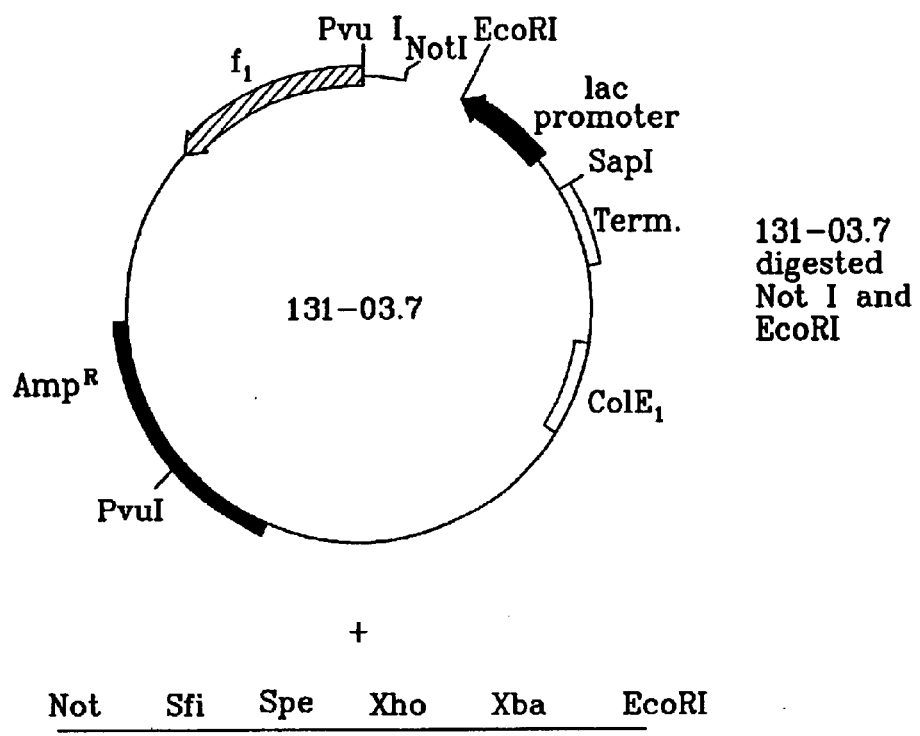
FIG. 7 schematically illustrates the insertion of multiple cloning sites.
Figure 7:
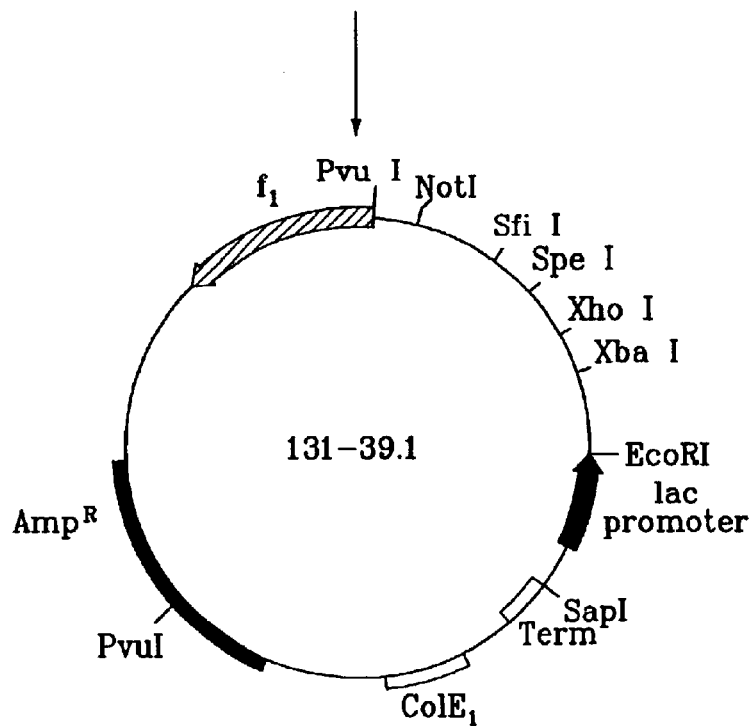

Oligonucleotides containing the Xba I, XhoI, SpeI and Sfi sites were then inserted into intermediate plasmid p131-03.7.(See FIG. 7.)

Intermediate vector p131-03.7 was digested with EcoR I and Not I and then gel purified. Then overlapping oligonucleotides containing the Xba I, Xho I, Spe I and Sfi I sites were ligated into the p131-03.7 backbone. The oligonucleotides inserted were:

> 5' AAT TCA CAT CTA GAT ATC TCG AGT CAA TAC TAG TGG CCA GGC CGG CCA GC 3' (SEQ. ID. NO. 7);

and

> 5' GGC CGC TGG CCG GCC TGG CCA CTA GTA TTG ACT CGA GAT ATC TAG ATG TG 3' (SEQ. ID. NO. 8).

Figure 8C:
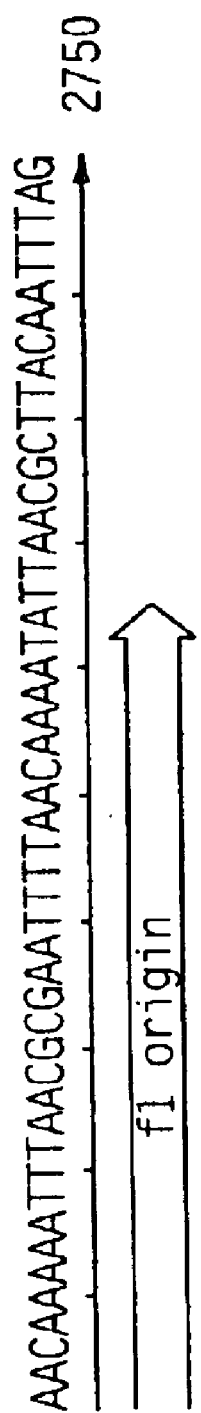

The resulting intermediate plasmid (designated p131-39.1) was sequenced and analyzed to determine its identity. The sequence (Seq. ID No. 21) of intermediate plasmid p131-39.1 is shown in FIGS. 8A–C.

Construction of Nucleotide Sequence Encoding Display Protein

Single stranded DNA from phage f1 (ATCC #15766-B2) was used as a template for the cloning of gene III. (See FIG. 9.)

The primers used were:

> 5' AGT GGC CAG GCC GGC CTT GAA ACT GTT GAA AGT TGT TTA GCA AA 3' (SEQ. ID. NO. 9)

which contains the Sfi I site, bases to maintain the coding frame and a portion of gene III; and > 5 TCT GCG GCC GCT TAG CTA GCT TAA GAC TCT TTA TTA CGC AGT ATG TTA GCA 3' (SEQ. ID. NO. 10);

which contains the end of gene III in which an internal ribosome binding site ordinarily used for the next downstream gene has been removed by changing a silent third base position in the corresponding codon. This oligonucleotide also contains a stop codon, Nhe I site for potential use in removal of the fusion, a second stop codon for use with the fusion, and the Not I site for cloning. The PCR fragment was digested with Sfi I and Not I and inserted into p131-39.1 digested with Sfi I and Not I to create intermediate vector p131-44.2.The integrity of the gene III region and flanking sequences was confirmed by sequence analysis.

Creation of the Upstream Transcriptional Control Cassette

Plasmid 131-39.1 was utilized as a shuttle vector for cloning the oligonucleotides containing the ompA signal peptide coding sequence. The upstream transcriptional control cassette was generated within intermediate plasmid 131-39.1 by inserting a pair of oligonucleotides which contain EcoR I, the ompA signal peptide leader, followed by a Sac I site, a small stuffer region, and a ribosome binding site. (See FIG. 9.) The oligonucleotides used were:

Eco Xba:

> 5' AAT TCA AGG AGT TAA TTA TGA AAA AAA CCG CGA TTG CGA TTG CGG TGG CGC TGG CGG GCT TTG CGA CCG TGG CCC AGG CGG CCG AGC TCA TCT T 3' (SEQ. ID. NO. 11);

and

Xba Eco:

> 5' CTA GAA GAT GAG CTC GGC CGC CTG GGC CAC GGT CGC AAA GCC CGC CAG CGC CAC CGC AAT CGC AAT CGC GGT TTT TTT CAT AAT TAA CTC CTT G 3' (SEQ. ID. NO. 12).

The RBS and leader sequences included in the upstream transcriptional control cassette are optimized for use in *E. coli*. These novel sequences are:

> 5' AAG GAG 3' (Seq. ID No.13)

for the RBS; and

> 5' ATG AAA AAA ACC GCG ATT GCG ATT GCG GTG GCG CTG GCG GGC TTT GCG ACC GTG GCC CAG GCG GCC 3' (Seq. ID No. 14)

for the ompA leader. The resulting plasmid was sequenced to confirm the identity of the insert and digested at the EcoRI and XbaI sites to generate a 94 bp fragment which is the upstream transcriptional control cassette.

Creation of the Downstream Transcriptional Control Cassette

Intermediate plasmid 131-39.1 was utilized as a shuttle vector for cloning the oligonucleotides containing the pelB signal peptide coding sequence. The downstream transcriptional control cassette was generated within intermediate plasmid 131-39.1 by inserting a pair of oligonucleotides containing the pelB signal peptide, Xba I, site, and a ribosome binding site. The oligonucleotides used were:

XbaXho:

> 5' CTA GAT ATA ATT AAG GAG ATA AAT ATG AAA TAT CTG CTG CCG ACC GCG GCG GCG GGC CTG CTG CTG CTG GCG GCG CAG CCG GCG ATG GCGC 3' (SEQ. ID. NO. 15);

and

XhoXba:

5' TCG AGC GCC ATC GCC GGC TGC GCC GCC AGC AGC
AGC AGG CCC GCC GCC GCG GTC GGC AGC AGA TAT
TTC ATA TTT ATC TCC TTA ATT
ATA T 3' (SEQ. ID. NO. 16).

The novel pelB leader sequence was optimized for use in *E. coli* and had the sequence 5' TAT GAA ATA TCT GCT GCC GAC CGC GGC GGC GGG
CCT GCT GCT GCT GGC GGC GCA GCC GGC GAT GGC
G 3' (Seq. ID No. 17).

The resulting plasmid was sequenced to confirm the identity of the insert and digested at the XbaI and XhoI sites to generate a 91 bp fragment which is the downstream transcriptional control cassette.

Construction of pAx131 Vector

Figure 9:
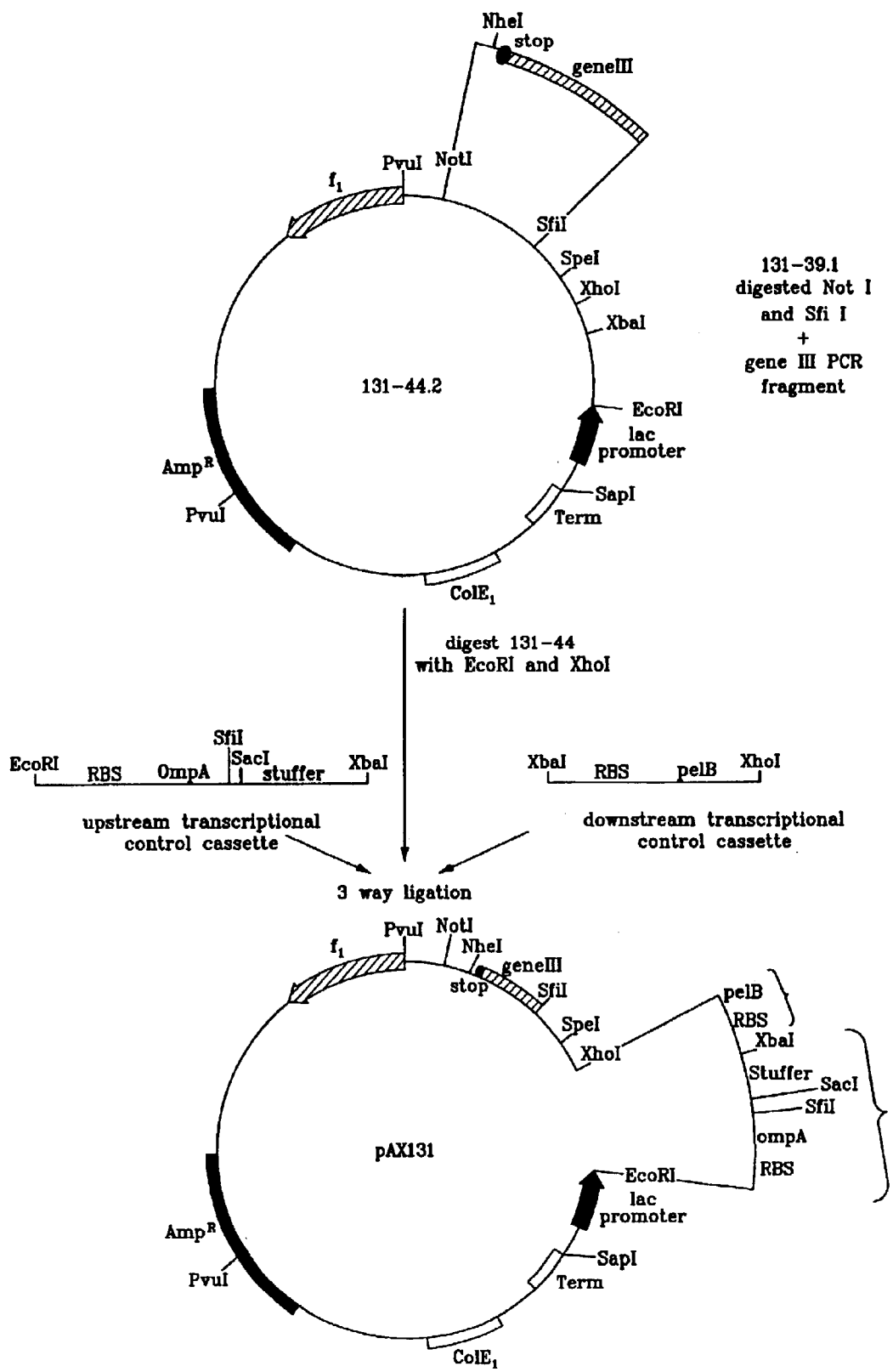
FIG. 9 schematically illustrates the insertion of the nucleotide sequence encoding the display protein and the two transcriptional control cassettes.
Figure 10:
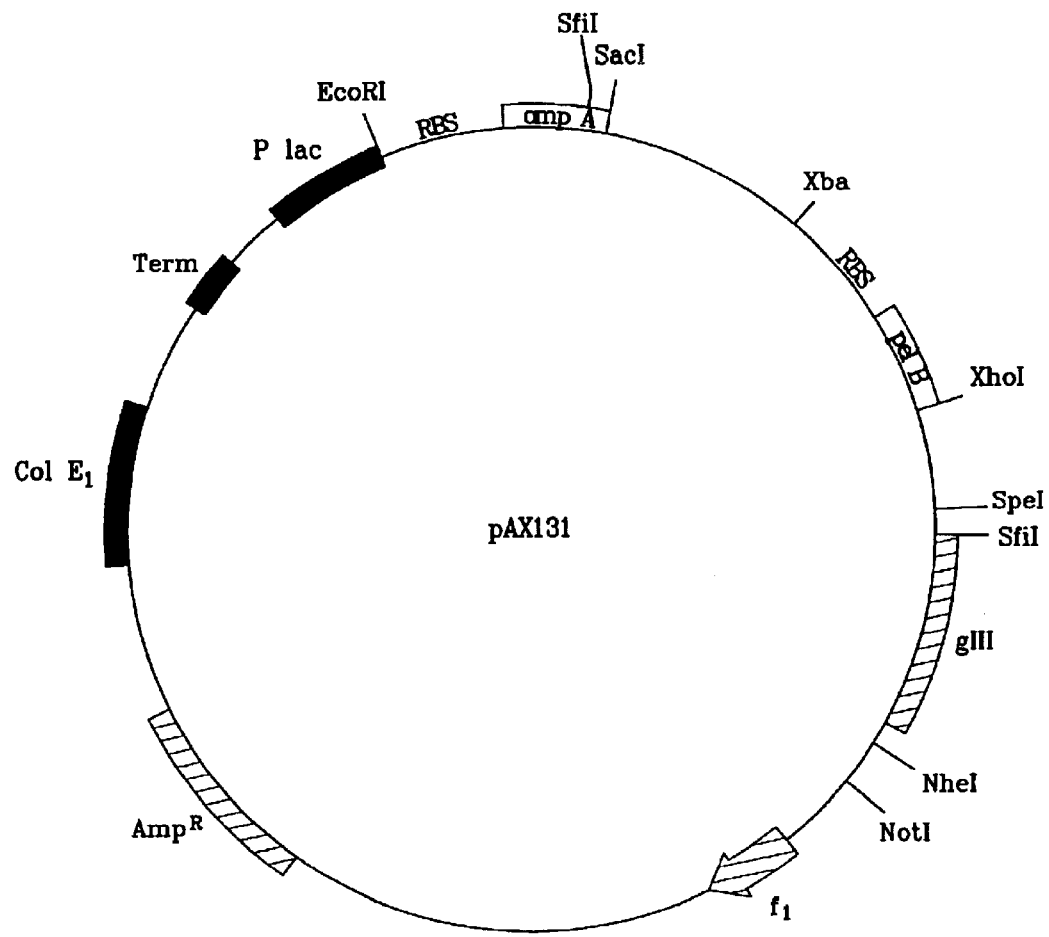
FIG. 10 is a map of plasmid pAX131.
Figure 11B:
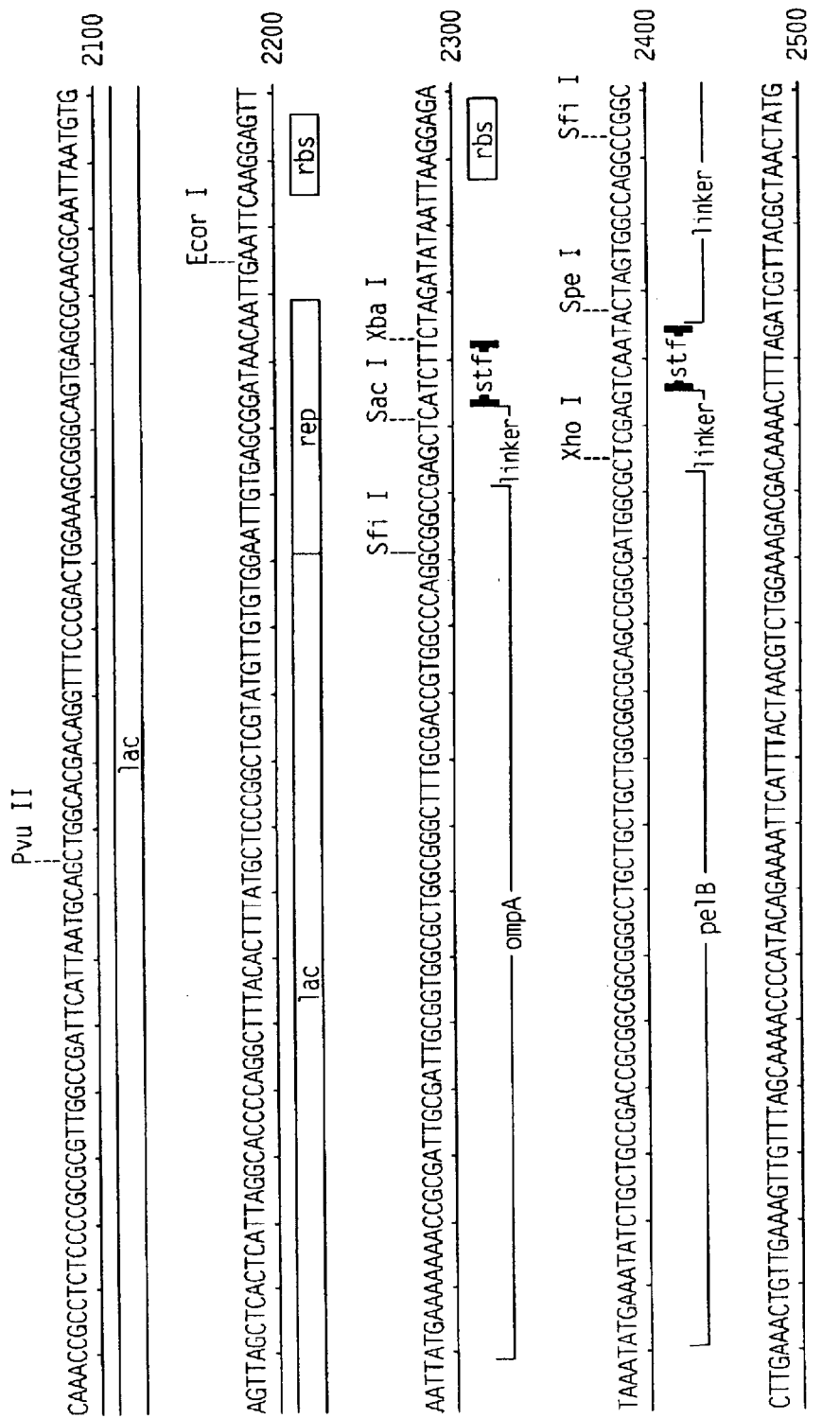
Figure 11C:
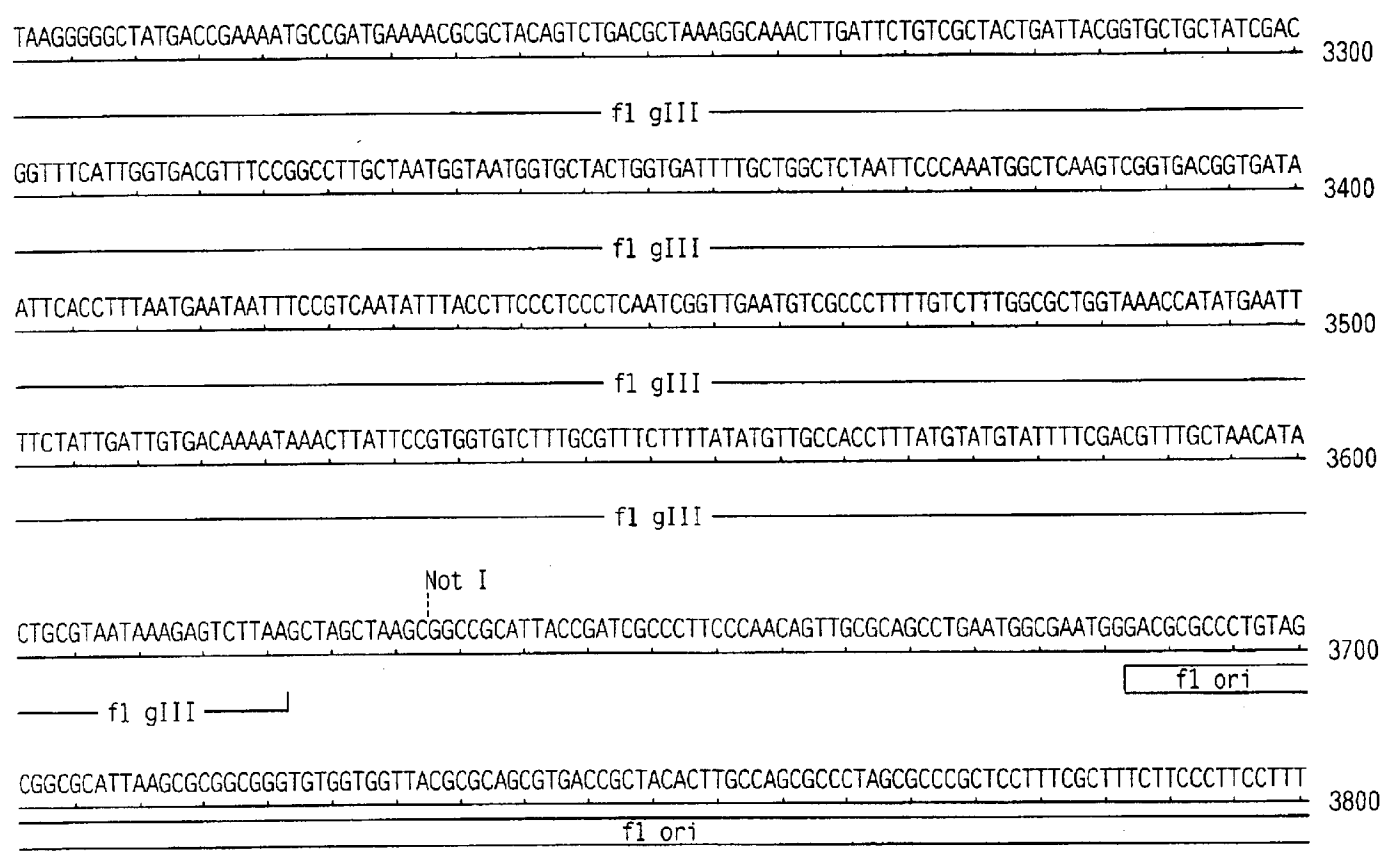
Figure 12A:
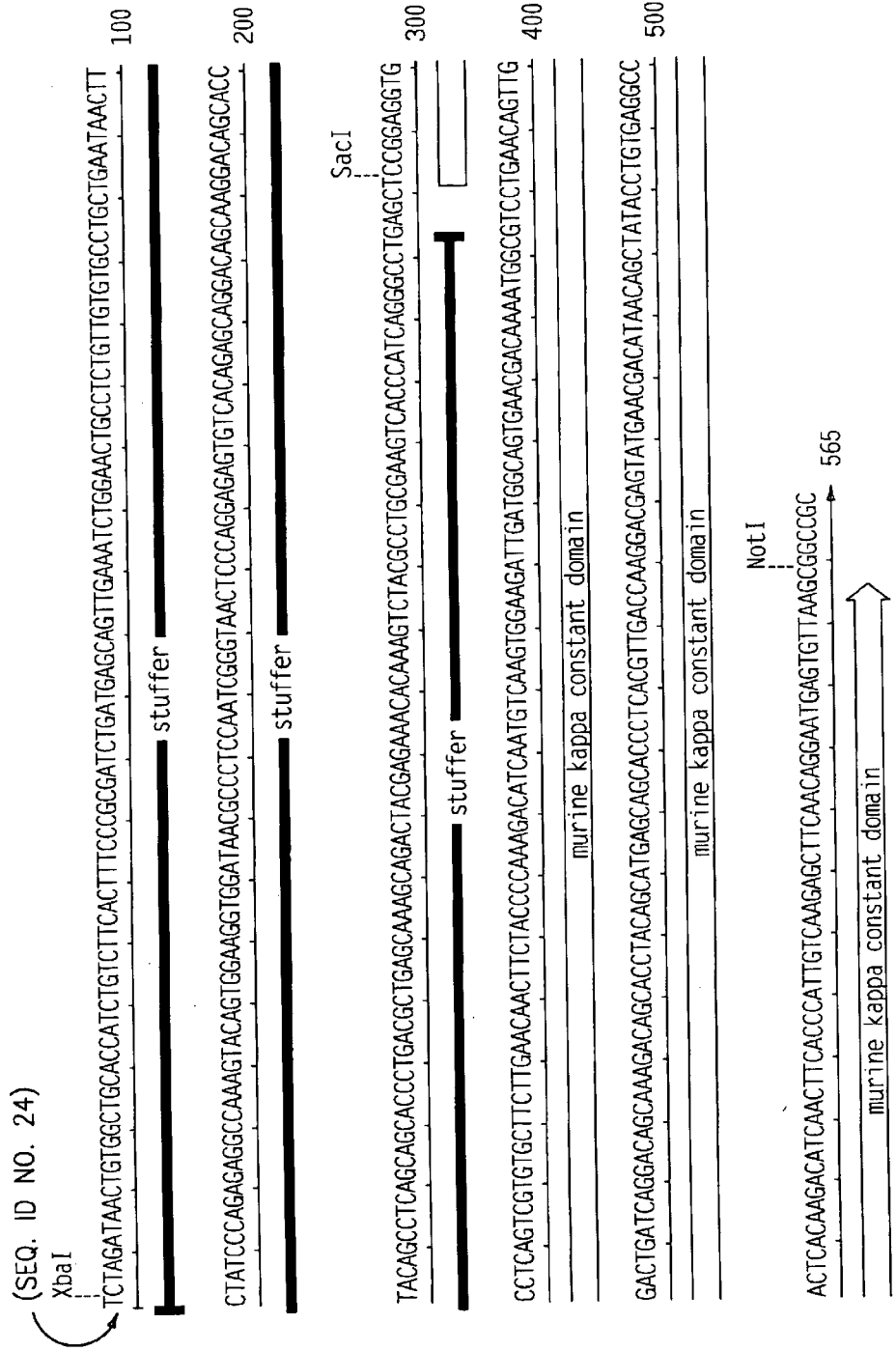
FIGS. 12A–G show the nucleic acid sequences of illustrative stuffer sequences.
Figure 12B:
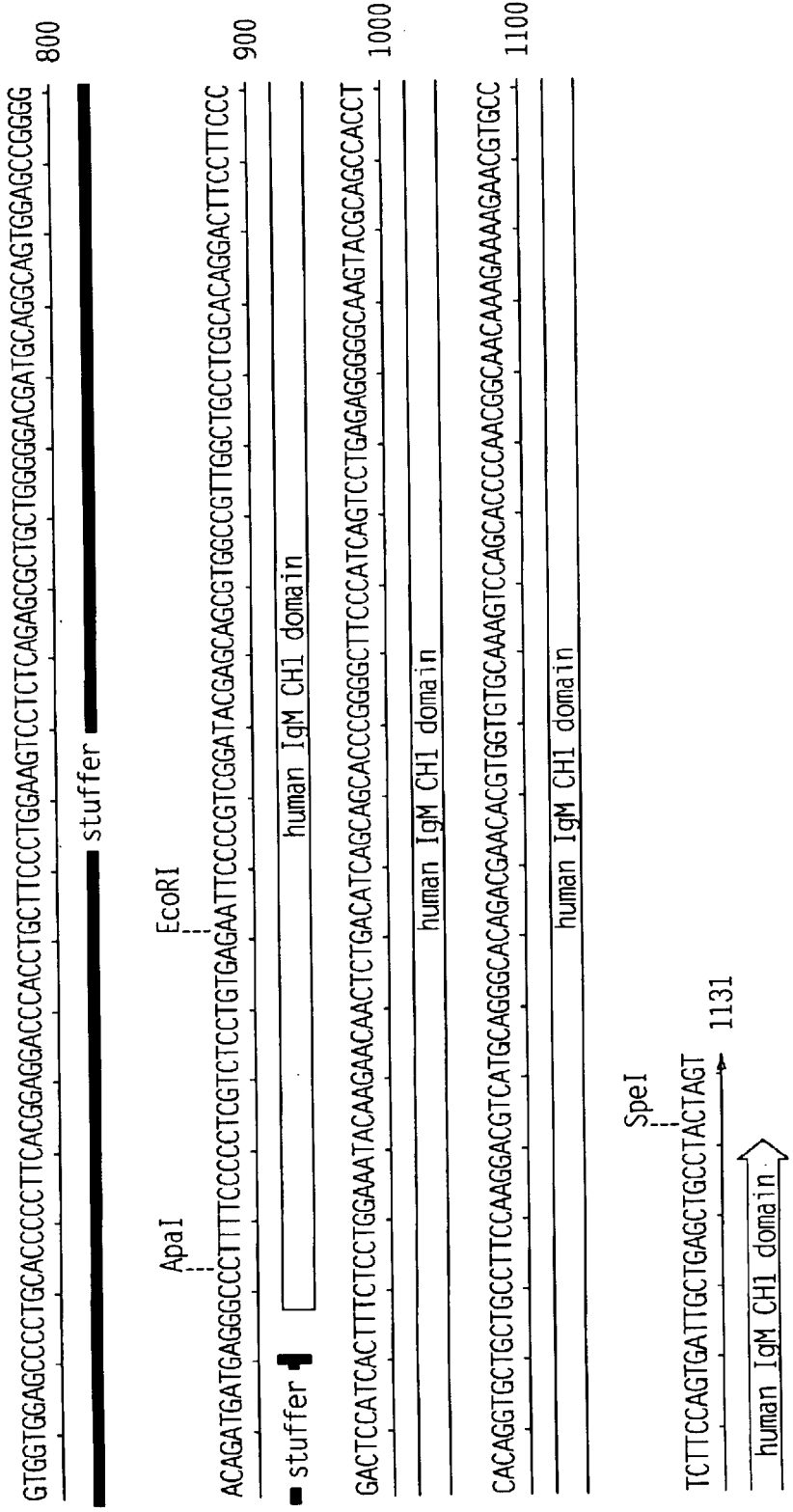
Figure 12C:
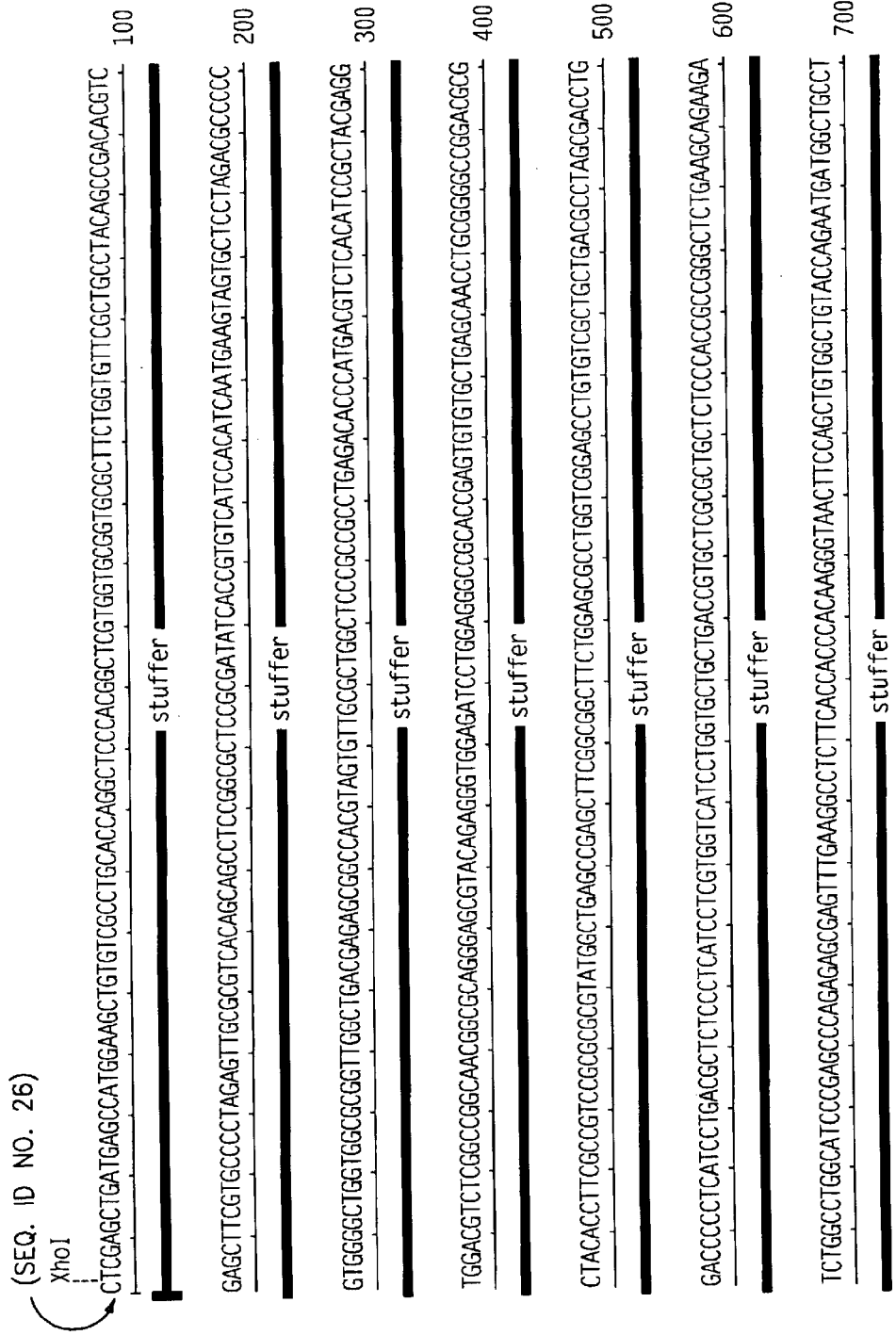
Figure 12C:
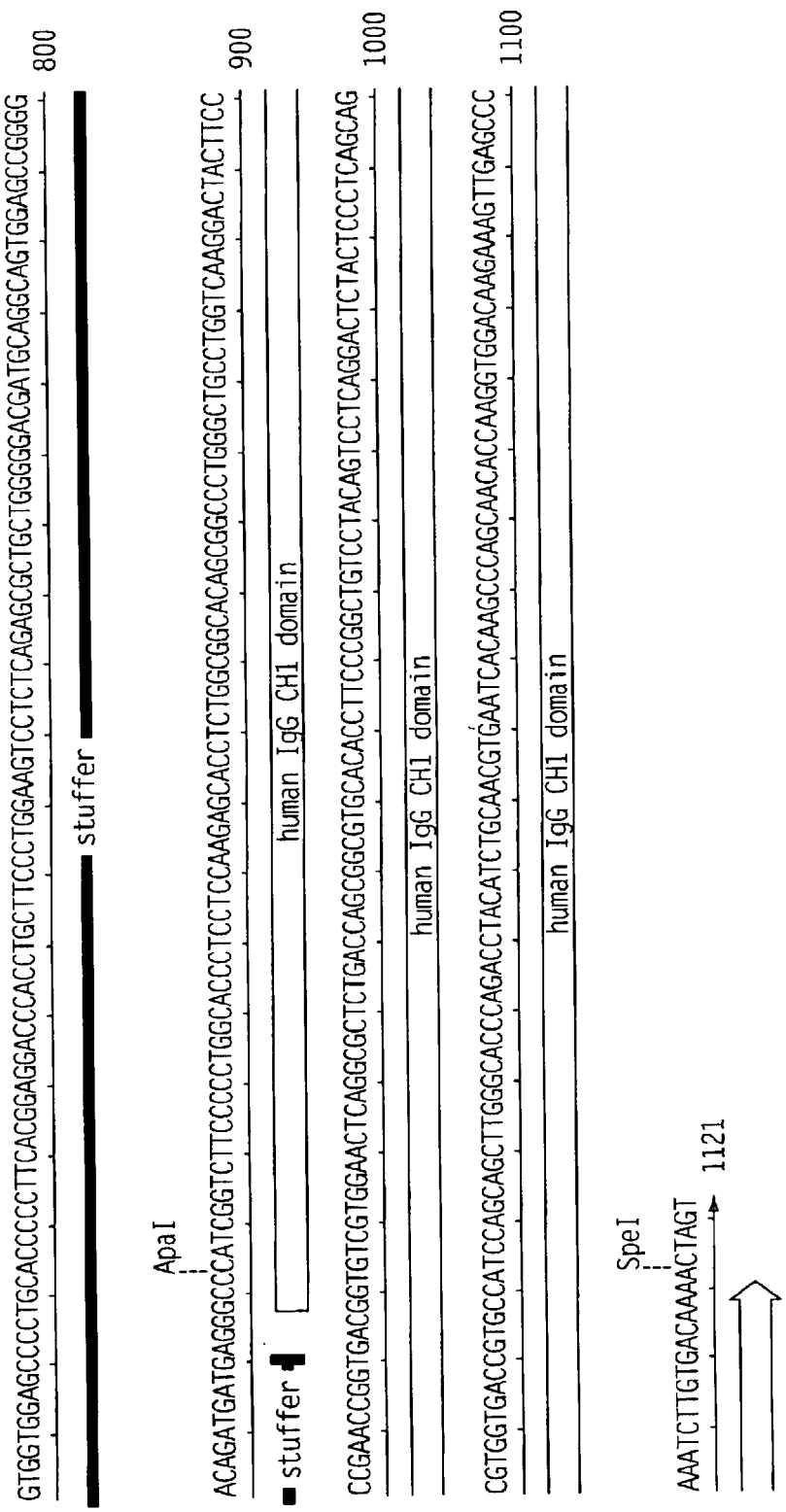
Figure 12D:
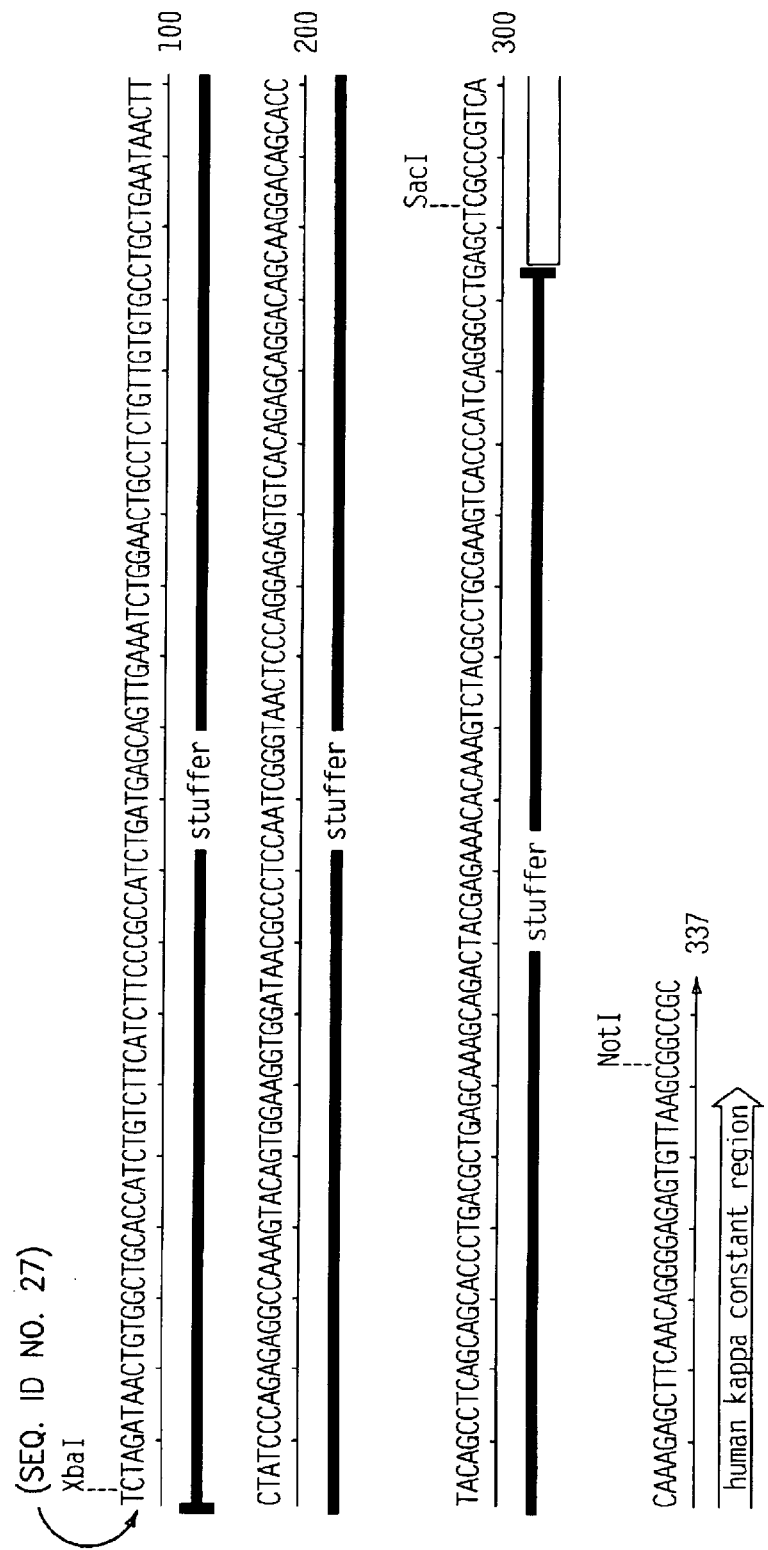
Figure 12E:
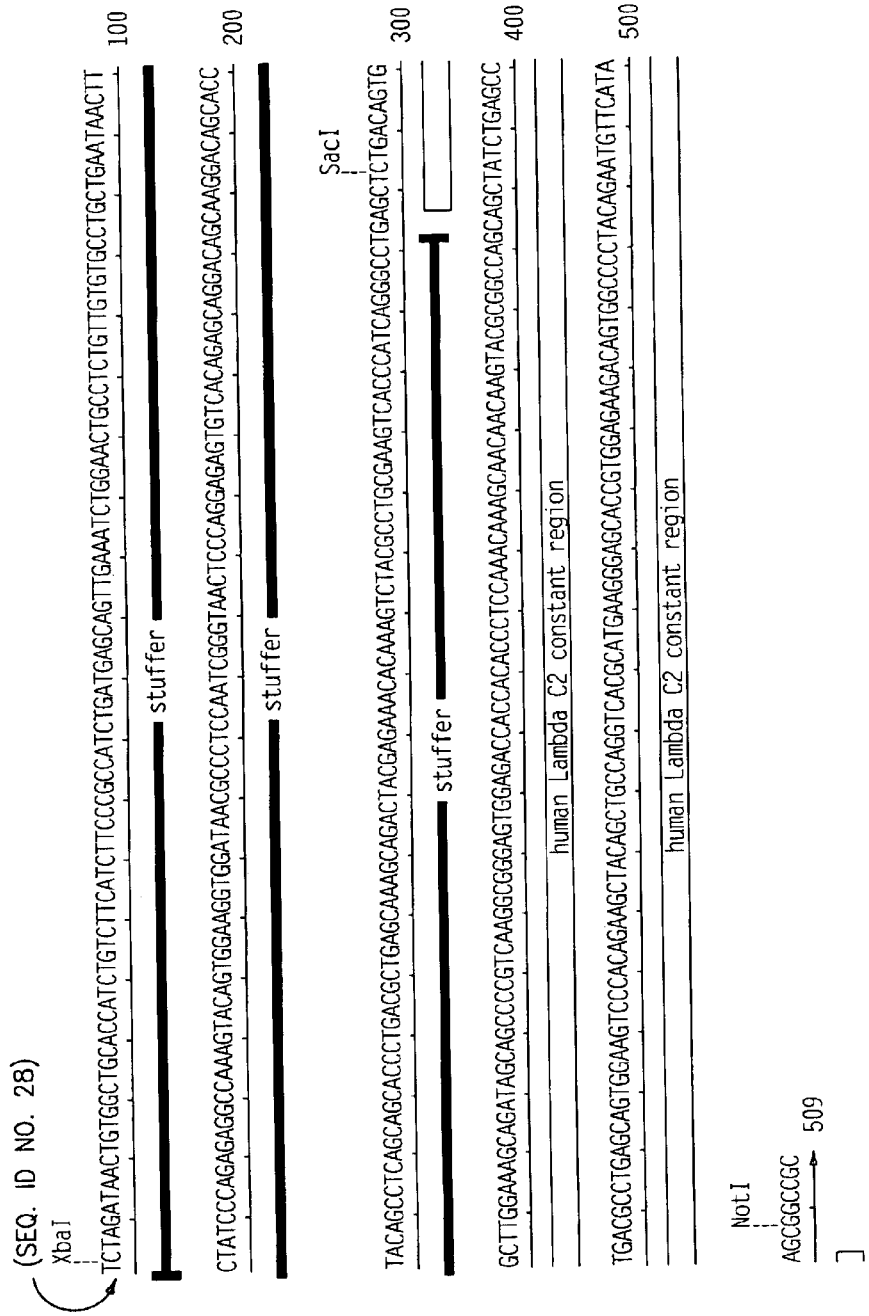
Figure 12F:
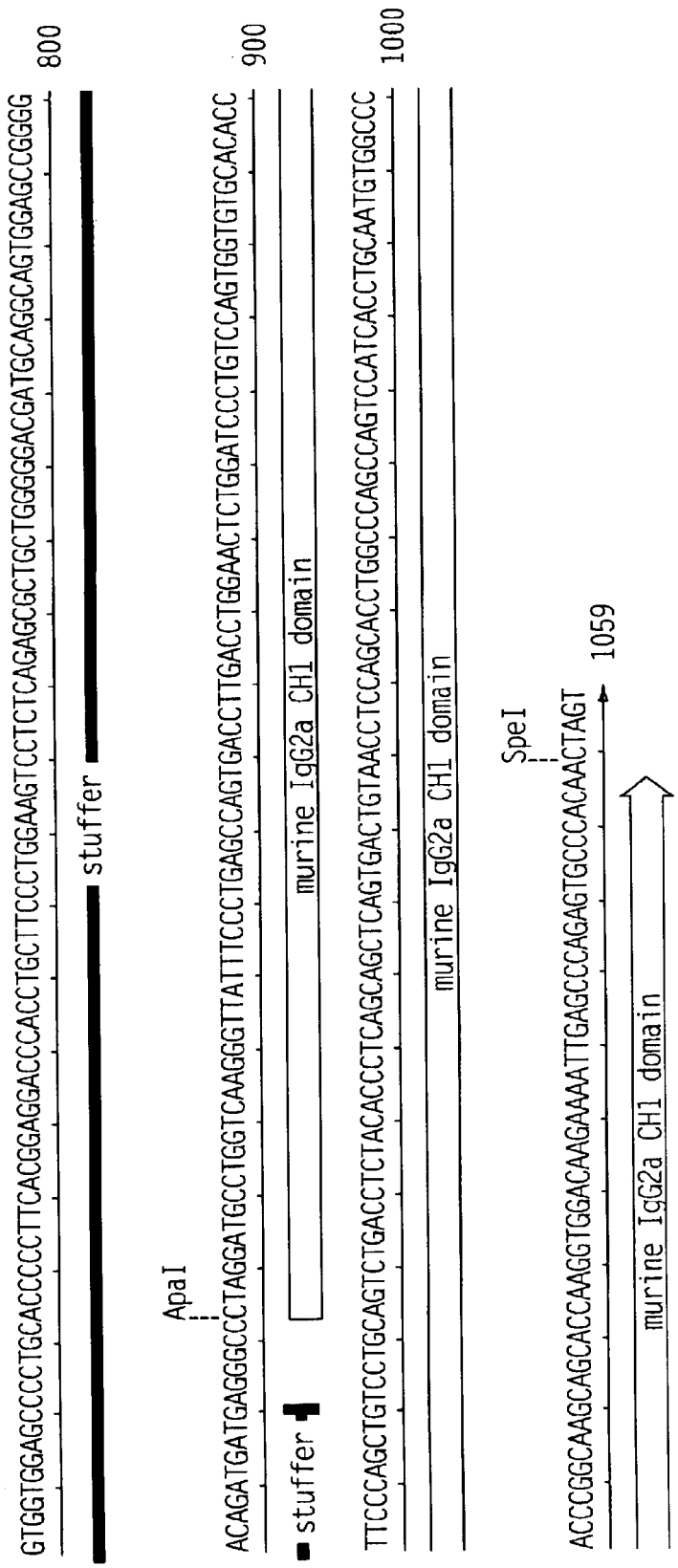
Figure 12G:
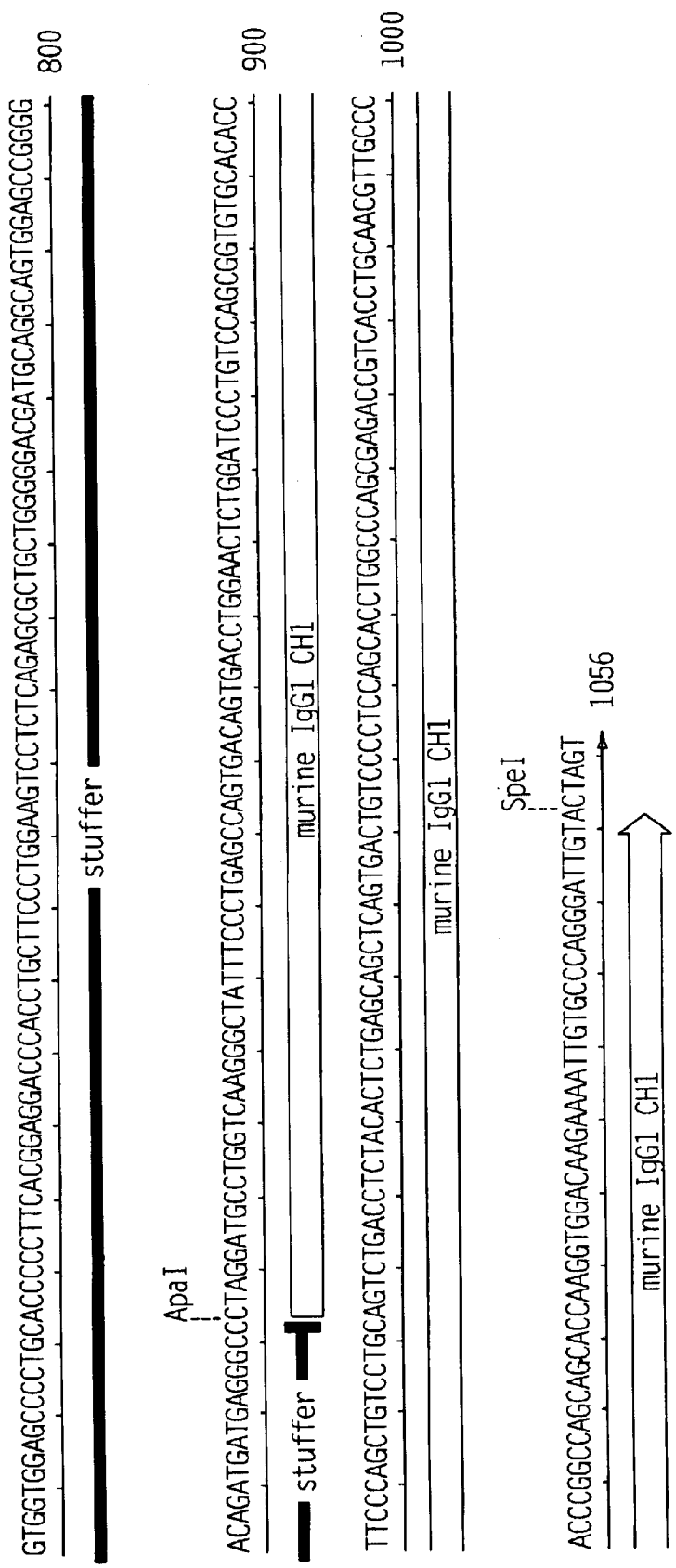

The upstream transcriptional control cassette and the downstream transcriptional control cassette were combined with intermediate plasmid p131-44.2 digested with EcoRI and XhoI in a 3-way ligation reaction to produce pAX131 (See FIG. 9). FIG. 10 is a map of the resulting pAX131 vector. The pAX131 was analyzed to determine its nucleic acid sequence (SEQ. ID. NO. 18) which is shown in FIGS. 11A–D.

EXAMPLE 2

Insertion of an alternate upstream transcriptional control cassette

PAX131 vector was digested with Not I restriction enzyme. The resulting DNA overhangs were then filled in with Klenow fragment Polymerase to blunt end the DNA followed by ligation. This was performed to remove the existing Not I site. The Not I deleted PAX131 vector was digested with EcoR I/Xba I, and ligated with a duplexed oligo containing EcoR I and Spe I overhangs (Xba I, and Spe I have compatible ends).

Eco/Spe oligo:

5' AAT TCA AGG AGT TAA TTA TGA AAA AAA CCG CGA
TTG CGA TTG CGG TGG CGC TGG CGG GCT TTG CGA
CCG TGG CCC AGG CGG CCT CTA GAA TCT GCG GCC
GCA 3' (SEQ. ID NO. 22)

Spe/Eco oligo:

5' CTA GTG CGG CCG CAG ATT CTA GAG GCC GCC TGG
GCC ACG GTC GCA AAG CCC GCC AGC GCC ACC GCA
ATC GCA ATC GCG GTT TTT TTC ATA ATT AAC TCC
TTG 3' (SEQ. ID NO. 23)

Figure 13B:
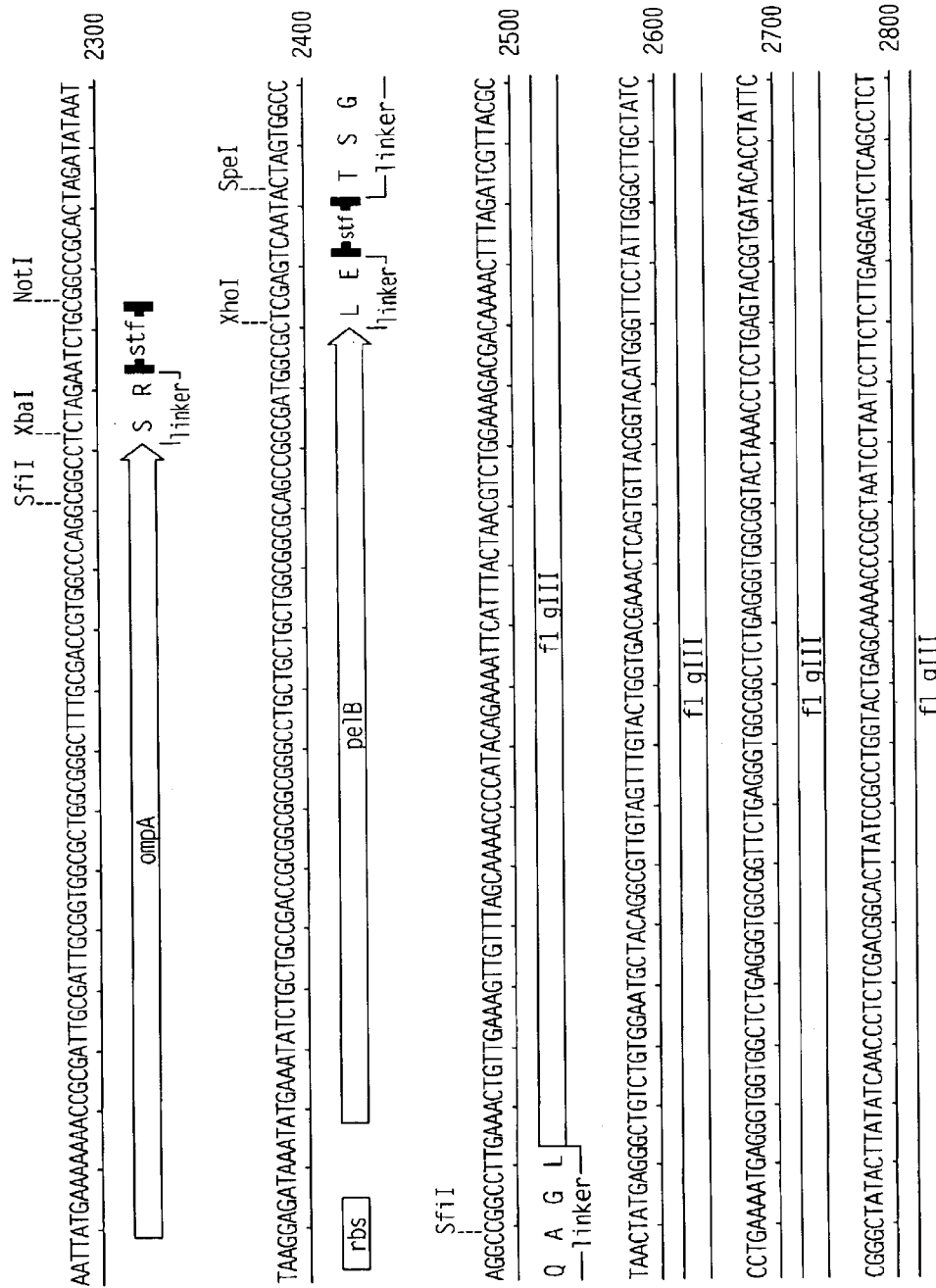
Figure 13C:
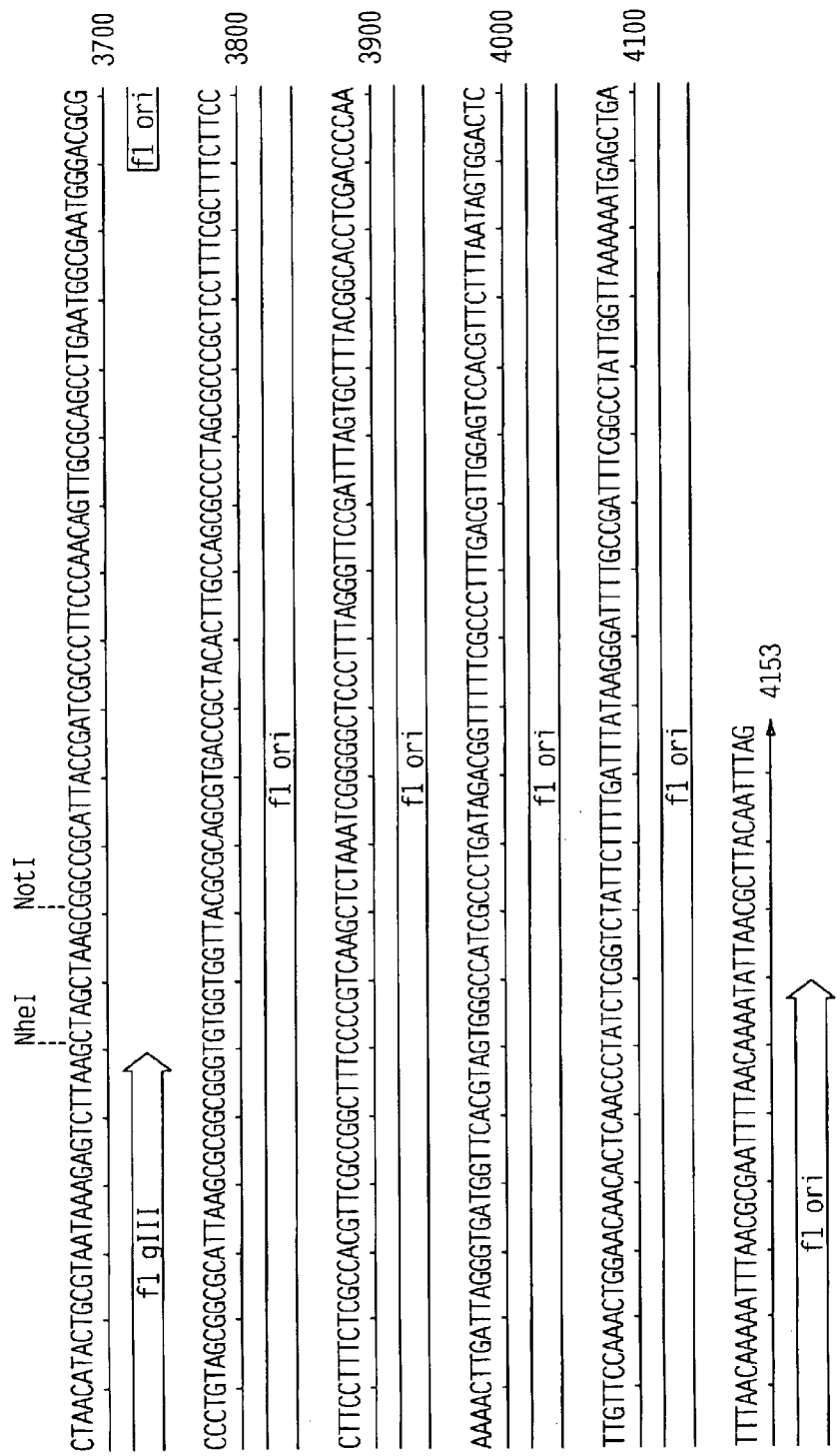

The resulting vector (pAX131 Xba/Not) had Xba I, and Not I sites for cloning of a gene, such as light chains, rather than Sac I and Xba I. FIGS. 13A–C show the nucleic acid sequence for vector (pAX131 Xba/Not.

It is contemplated that the present novel vectors can be used in connection with the production and screening of libraries made in accordance with conventional phage display technologies. Both natural and synthetic antibody repertoires have been generated as phage displayed libraries. Natural antibodies can be cloned from B-cell mRNA isolated from peripheral blood lymphocytes, bone marrow, spleen, or other lymphatic tissue of a human or non-human donor. Donors with an immune response to the antigen(s) of interest can be used to create immune antibody libraries. Alternatively, non-immune libraries may be generated from donors by isolating naive antibody B cell genes. PCR using antibody specific primers on the $18^{st}$ strand cDNA allows the isolation of light chain and heavy chain antibody fragments which can then be cloned into the display vector.

Synthetic antibodies or antibody libraries can be made up in part or entirely with regions of synthetically derived sequence. Library diversity can be engineered within variable regions, particularly within CDRs, through the use of degenerate oligonucleotides. For example, a single Fab gene may be modified at the heavy chain CDR3 position to contain random nucleotide sequences. The random sequence can be introduced into the heavy chain gene using an oligonucleotide which contains the degenerate coding region in an overlap PCR approach. Alternatively, degenerate oligo cassettes can be cloned into restriction sites that flank the CDR(s) to create diversity. The resulting library generated by this or other approaches can then be cloned into a display vector in accordance with this disclosure.

Upon introduction of the display library into bacteria, phage particles will be generated that have antibody displayed on the surface. The resulting collection of phage-displayed antibodies can be selected for those with the ability to bind to the antigen of interest using techniques known to those skilled in the art. Antibodies identified by this system can be used therapeutically, as diagnostic reagents, or as research tools.

It is contemplated that single and double stranded versions of the vectors described herein are within the scope of the present invention. It is well within the purview of those skilled in the art to prepare either single or double stranded vectors having the features described herein.

It will be understood that various modifications may be made to the embodiments described herein. For example, as those skilled in the art will appreciate, a first gene encoding a fusion protein having an antibody light chain to be fused to and displayed by pVIII and a second gene encoding a heavy chain Fd can be inserted into the vector at the newly created restriction site to provide effective antibody display. Therefore, the above description should not be construed as limiting, but merely as exemplifications of preferred embodiments. Those skilled in the art will envision other modifications within the scope and spirit of the claims appended hereto.

We claim:

1. A phagemid vector comprising:
   a selectable marker;
   a ColE1 origin;
   an f1 origin; and
   after the ColE1 origin but before the f1 origin, further comprising the following features:
   a bacterial transcription terminator;
   a promoter,
   a first ribosomal binding site;
   a first leader sequence;
   a first cloning region;
   a second ribosomal binding site;
   a second leader sequence;
   a second cloning region for receiving a gene encoding a polypeptide to be displayed; and
   a nucleotide sequence encoding a product that enables display of a polypeptide on the surface of a phagemid particle.

2. A phagemid vector as in claim 1 wherein at least one of the first or second ribosomal binding sites comprises Seq. ID No. 13.

3. A phagemid vector as in claim 1 wherein at least one of the first or second leader sequences comprises a sequence selected from the group consisting of Seq. ID No. 14 and Seq. ID No. 17.

4. A phagemid vector as in claim 1 wherein the nucleotide sequence encoding a product encodes a protein selected from the group consisting of pIII and pVIII.

5. A phagemid vector as in claim 1 wherein the nucleotide sequence encoding a product encodes a truncated pIII.

6. A phagemid vector as in claim 1 wherein the nucleotide sequence encoding a product encodes a synthetic pIII.

7. A phagemid vector as in claim 1 wherein the selectable marker is selected from the group consisting of ampicillin resistance, chloramphenicol transferase resistance, tetracycline resistance and kanamycin resistance.

8. A phagemid vector comprising Seq. ID No. 18.

9. A vector comprising a sequence selected from the group consisting of Seq. ID Nos. 19, 20 and 21.

* * * * *

SEQUENCE LISTING

<160> NUMBER OF SEQ ID NOS: 31

<210> SEQ ID NO 1
<211> LENGTH: 23
<212> TYPE: DNA
<213> ORGANISM: artificial sequence
<220> FEATURE:
<223> OTHER INFORMATION: primer

```
<400> SEQUENCE: 1
aaccgtatta ccgcctttga gtg                                          23

<210> SEQ ID NO 2
<211> LENGTH: 34
<212> TYPE: DNA
<213> ORGANISM: artificial sequence
<220> FEATURE:
<223> OTHER INFORMATION: primer

<400> SEQUENCE: 2
cctgaattca attgttatcc gctcacaatt ccac                              34

<210> SEQ ID NO 3
<211> LENGTH: 21
<212> TYPE: DNA
<213> ORGANISM: artificial sequence
<220> FEATURE:
<223> OTHER INFORMATION: oligonucleotide

<400> SEQUENCE: 3
cggtaatgcg ccgctacat g                                             21

<210> SEQ ID NO 4
<211> LENGTH: 27
<212> TYPE: DNA
<213> ORGANISM: artificial sequence
<220> FEATURE:
<223> OTHER INFORMATION: oligonucleotide

<400> SEQUENCE: 4
aattcatgta gcggccgcat taccgat                                      27

<210> SEQ ID NO 5
<211> LENGTH: 58
<212> TYPE: DNA
<213> ORGANISM: artificial sequence
<220> FEATURE:
<223> OTHER INFORMATION: oligonucleotide

<400> SEQUENCE: 5
agcgtacccg ataaaagcgg cttcctgaca ggaggccgtt ttgttttgca gcccacct    58

<210> SEQ ID NO 6
<211> LENGTH: 58
<212> TYPE: DNA
<213> ORGANISM: artificial sequence
<220> FEATURE:
<223> OTHER INFORMATION: oligonucleotide

<400> SEQUENCE: 6
gctaggtggg ctgcaaaaca aaacggcctc ctgtcaggaa gccgctttta tcgggtac    58

<210> SEQ ID NO 7
<211> LENGTH: 50
<212> TYPE: DNA
<213> ORGANISM: artificial sequence
<220> FEATURE:
<223> OTHER INFORMATION: oligonucleotide

<400> SEQUENCE: 7
aattcacatc tagatatctc gagtcaatac tagtggccag gccggccagc             50

<210> SEQ ID NO 8
<211> LENGTH: 50
```

```
<212> TYPE: DNA
<213> ORGANISM: artificial sequence
<220> FEATURE:
<223> OTHER INFORMATION: oligonucleotide

<400> SEQUENCE: 8
ggccgctggc cggcctggcc actagtattg actcgagata tctagatgtg        50

<210> SEQ ID NO 9
<211> LENGTH: 44
<212> TYPE: DNA
<213> ORGANISM: artificial sequence
<220> FEATURE:
<223> OTHER INFORMATION: primer

<400> SEQUENCE: 9
agtggccagg ccggccttga aactgttgaa agttgtttag caaa              44

<210> SEQ ID NO 10
<211> LENGTH: 51
<212> TYPE: DNA
<213> ORGANISM: artificial sequence
<220> FEATURE:
<223> OTHER INFORMATION: primer

<400> SEQUENCE: 10
tctgcggccg cttagctagc ttaagactct ttattacgca gtatgttagc a       51

<210> SEQ ID NO 11
<211> LENGTH: 94
<212> TYPE: DNA
<213> ORGANISM: artificial sequence
<220> FEATURE:
<223> OTHER INFORMATION: oligonucleotide

<400> SEQUENCE: 11
aattcaagga gttaattatg aaaaaaaccg cgattgcgat tgcggtggcg ctggcgggct    60
ttgcgaccgt ggcccaggcg gccgagctca tctt                              94

<210> SEQ ID NO 12
<211> LENGTH: 94
<212> TYPE: DNA
<213> ORGANISM: artificial sequence
<220> FEATURE:
<223> OTHER INFORMATION: oligonucleotide

<400> SEQUENCE: 12
ctagaagatg agctcggccg cctgggccac ggtcgcaaag cccgccagcg ccaccgcaat    60
cgcaatcgcg gttttttttca taattaactc cttg                             94

<210> SEQ ID NO 13
<211> LENGTH: 6
<212> TYPE: DNA
<213> ORGANISM: artificial sequence
<220> FEATURE:
<223> OTHER INFORMATION: RBS

<400> SEQUENCE: 13 aaggag                                                             6

<210> SEQ ID NO 14
<211> LENGTH: 66
<212> TYPE: DNA
<213> ORGANISM: artificial sequence
<220> FEATURE:
```

```
<223> OTHER INFORMATION: ompA leader

<400> SEQUENCE: 14
atgaaaaaaa ccgcgattgc gattgcggtg gcgctggcgg gctttgcgac cgtggcccag      60
gcggcc                                                                66

<210> SEQ ID NO 15
<211> LENGTH: 91
<212> TYPE: DNA
<213> ORGANISM: artificial sequence
<220> FEATURE:
<223> OTHER INFORMATION: oligonucleotide

<400> SEQUENCE: 15
ctagatataa ttaaggagat aaatatgaaa tatctgctgc cgaccgcggc ggcgggcctg      60
ctgctgctgg cggcgcagcc ggcgatggcg c                                    91

<210> SEQ ID NO 16
<211> LENGTH: 91
<212> TYPE: DNA
<213> ORGANISM: artificial sequence
<220> FEATURE:
<223> OTHER INFORMATION: oligonucleotide

<400> SEQUENCE: 16
tcgagcgcca tcgccggctg cgccgccagc agcagcaggc ccgccgccgc ggtcggcagc      60
agatatttca tatttatctc cttaattata t                                    91

<210> SEQ ID NO 17
<211> LENGTH: 67
<212> TYPE: DNA
<213> ORGANISM: artificial sequence
<220> FEATURE:
<223> OTHER INFORMATION: pelB leader

<400> SEQUENCE: 17
tatgaaatat ctgctgccga ccgcggcggc gggcctgctg ctgctggcgg cgcagccggc      60
gatggcg                                                               67

<210> SEQ ID NO 18
<211> LENGTH: 4154
<212> TYPE: DNA
<213> ORGANISM: artificial sequence
<220> FEATURE:
<223> OTHER INFORMATION: plasmid vector

<400> SEQUENCE: 18
gtggcacttt tcggggaaat gtgcgcggaa cccctatttg tttatttttc taaatacatt      60
caaatatgta tccgctcatg agacaataac cctgataaat gcttcaataa tattgaaaaa     120
ggaagagtat gagtattcaa catttccgtg tcgcccttat tccctttttt gcggcatttt     180
gccttcctgt ttttgctcac ccagaaacgc tggtgaaagt aaaagatgct gaagatcagt     240
tgggtgcacg agtgggttac atcgaactgg atctcaacag cggtaagatc cttgagagtt     300
ttcgccccga agaacgtttt ccaatgatga gcacttttaa agttctgcta tgtggcgcgg     360
tattatcccg tattgacgcc gggcaagagc aactcggtcg ccgcatacac tattctcaga     420
atgacttggt tgagtactca ccagtcacag aaaagcatct tacggatggc atgacagtaa     480
gagaattatg cagtgctgcc ataaccatga gtgataacac tgcggccaac ttacttctga     540
caacgatcgg aggaccgaag gagctaaccg cttttttgca acatggggg gatcatgtaa     600
```

-continued

```
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca gtttactca tatatacttt     1020 agattgattt aaaacttcat ttttaattta aaaggatcta ggtgaagatc cttttttgata   1080 atctcatgac caaaatccct taacgtgagt tttcgttcca ctgagcgtca gaccccgtag    1140
aaaagatcaa aggatcttct tgagatcctt ttttctgcg cgtaatctgc tgcttgcaaa     1200
caaaaaaacc accgctacca gcggtggttt gtttgccgga tcaagagcta ccaactcttt    1260
ttccgaaggt aactggcttc agcagagcgc agataccaaa tactgtcctt ctagtgtagc    1320
cgtagttagg ccaccacttc aagaactctg tagcaccgcc tacatacctc gctctgctaa    1380
tcctgttacc agtggctgct gccagtggcg ataagtcgtg tcttaccggg ttggactcaa    1440
gacgatagtt accggataag cgcagcggt cgggctgaac gggggggttcg tgcacacagc    1500 ccagcttgga gcgaacgacc tacaccgaac tgagatacct acagcgtgag ctatgagaaa    1560
gcgccacgct tcccgaaggg agaaaggcgg acaggtatcc ggtaagcggc agggtcggaa    1620
caggagagcg cacgagggag cttccagggg gaaacgcctg gtatctttat agtcctgtcg    1680
ggtttcgcca cctctgactt gagcgtcgat ttttgtgatg ctcgtcaggg gggcggagcc    1740 tatgaaaaa cgccagcaac gcggcctttt tacggttcct ggccttttgc tggccttttg     1800
ctcacatgtt ctttcctgcg ttatcccctg attctgtgga taaccgtatt accgcctttg    1860
agtgagctga taccgctcgc cgcagccgaa cgaccgagcg cagcgagtca gtgagcgagg    1920
aagcgtaccc gataaaagcg gcttcctgac aggaggccgt tttgttttgc agcccaccta    1980
gcggaagagc gcccaatacg caaaccgcct ctccccgcgc gttggccgat tcattaatgc    2040
agctggcacg acaggtttcc cgactggaaa gcgggcagtg agcgcaacgc aattaatgtg    2100
agttagctca ctcattaggc accccaggct ttacacttta tgctcccggc tcgtatgttg    2160
tgtggaattg tgagcggata caattgaat tcaaggagtt aattatgaaa aaaaccgcga    2220
ttgcgattgc ggtggcgctg gcgggctttg cgaccgtggc ccaggcggcc gagctcatct    2280
tctagatata attaaggaga taaatatgaa atatctgctg ccgaccgcgg cggcgggcct    2340
gctgctgctg gcgcgcagc cggcgatggc gctcgagtca atactagtgg ccaggccggc    2400
cttgaaactg ttgaaagttg tttagcaaaa ccccatacag aaaattcatt tactaacgtc    2460
tggaaagacg acaaaactt agatcgttac gctaactatg agggctgtct gtggaatgct    2520
acaggcgttg tagtttgtac tggtgacgaa actcagtgtt acggtacatg ggttcctatt    2580
gggcttgcta tccctgaaaa tgagggtggt ggctctgagg gtggcggttc tgagggtggc    2640
ggctctgagg gtggcggtac taaacctcct gagtacggtg atacacctat tccgggctat    2700
acttatatca accctctcga cggcacttat ccgcctggta ctgagcaaaa ccccgctaat    2760
cctaatcctt ctcttgagga gtctcagcct cttaatactt tcatgtttca gaataatagg    2820
ttccgaaata ggcaggggc attaactgtt tatacgggca ctgttactca aggcactgac    2880
cccgttaaaa cttattacca gtacactcct gtatcatcaa aagccatgta tgacgcttac    2940
```

```
tggaacggta aattcagaga ctgcgctttc cattctggct ttaatgagga tccattcgtt    3000
tgtgaatatc aaggccaatc gtctgacctg cctcaacctc ctgttaatgc tggcggcggc    3060
tctggtggtg gttctggtgg cggctctgag ggtggtggct ctgagggtgg cggttctgag    3120
ggtggcggct ctgagggtgg cggttccggt ggtggctctg gttccggtga ttttgattat    3180
gaaaagatgg caaacgctaa taaggggggct atgaccgaaa atgccgatga aaacgatgaa    3240
aacgcgctac agtctgacgc taaaggcaaa cttgattctg tcgctactga ttacggtgct    3300
gctatcgacg gtttcattgg tgacgtttcc ggccttgcta atggtaatgg tgctactggt    3360
gattttgctg gctctaattc ccaaatggct caagtcggtg acggtgataa ttcacccttta    3420 atgaataatt tccgtcaata tttaccttcc ctccctcaat cggttgaatg tcgcccttttt    3480 gtctttggcg ctggtaaacc atatgaattt tctattgatt gtgacaaaat aaacttattc    3540
cgtggtgtct ttgcgtttct tttatatgtt gccaccttta tgtatgtatt ttcgacgttt    3600
gctaacatac tgcgtaataa agagtcttaa gctagctaag cggccgcatt accgatcgcc    3660
cttcccaaca gttgcgcagc ctgaatggcg aatgggacgc gccctgtagc ggcgcattaa    3720
gcgcggcggg tgtggtggtt acgcgcagcg tgaccgctac acttgccagc gccctagcgc    3780
ccgctccttt cgctttcttc ccttcctttc tcgccacgtt cgccggcttt ccccgtcaag    3840
ctctaaatcg gggggctccct ttagggttcc gatttagtgc tttacggcac ctcgacccca    3900
aaaaacttga ttagggtgat ggttcacgta gtgggccatc gccctgatag acggtttttc    3960
gccctttgac gttggagtcc acgttcttta atagtggact cttgttccaa actggaacaa    4020
cactcaaccc tatctcggtc tattcttttg atttataagg gattttgccg atttcggcct    4080
attggttaaa aaatgagctg atttaacaaa aatttaacgc gaattttaac aaaatattaa    4140
cgcttacaat ttag                                                     4154

<210> SEQ ID NO 19
<211> LENGTH: 2654
<212> TYPE: DNA
<213> ORGANISM: artificial sequence
<220> FEATURE:
<223> OTHER INFORMATION: plasmid vector

<400> SEQUENCE: 19
ctaaattgta agcgttaata ttttgttaaa attcgcgtta aattttttgtt aaatcagctc      60 attttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt ttttgggggt cgaggtgccg taaagcacta atcggaacc ctaaagggag     300 cccccgattt agagcttgac ggggaaagcc ggcgaacgtg gcgagaaagg aagggaagaa     360
agcgaaagga gcgggcgcta gggcgctggc aagtgtagcg tcacgctgc gcgtaaccac     420 cacacccgcc gcgcttaatg cgccgctaca gggcgcgtcc cattcgccat tcaggctgcg     480
caactgttgg gaagggcgat cggtaatgcg gcgctacat gaattcaatt gttatccgct     540
cacaattcca cacaacatac gagccggaag cataaagtgt aaagcctggg gtgcctaatg     600
agtgagctaa ctcacattaa ttgcgttgcg ctcactgccc gctttccagt cgggaaacct     660
gtcgtgccag ctgcattaat gaatcggcca acgcgcgggg agaggcggtt tgcgtattgg     720
gcgctcttcc gcttcctcgc tcactgactc gctgcgctcg tcgttcggc tgcggcgagc     780 ggtatcagct cactcaaagg cggtaatacg gttatccaca gaatcagggg ataacgcagg     840
```

-continued

```
aaagaacatg tgagcaaaag gccagcaaaa ggccaggaac cgtaaaaagg ccgcgttgct      900 ggcgttttc cataggctcc gccccctga cgagcatcac aaaaatcgac gctcaagtca       960
gaggtggcga aacccgacag gactataaag ataccaggcg tttccccctg gaagctccct     1020
cgtgcgctct cctgttccga ccctgccgct taccggatac ctgtccgcct ttctcccttc     1080
gggaagcgtg cgctttctc atagctcacg ctgtaggtat ctcagttcgg tgtaggtcgt      1140
tcgctccaag ctgggctgtg tgcacgaacc ccccgttcag cccgaccgct gcgccttatc     1200
cggtaactat cgtcttgagt ccaacccggt aagacacgac ttatcgccac tggcagcagc     1260
cactggtaac aggattagca gagcgaggta tgtaggcggt gctacagagt tcttgaagtg     1320
gtggcctaac tacggctaca ctagaaggac agtatttggt atctgcgctc tgctgaagcc     1380
agttaccttc ggaaaaagag ttggtagctc ttgatccggc aaacaaacca ccgctggtag     1440
cggtggtttt tttgtttgca agcagcagat tacgcgcaga aaaaaaggat ctcaagaaga     1500
tcctttgatc ttttctacgg ggtctgacgc tcagtggaac gaaaactcac gttaagggat     1560
tttggtcatg agattatcaa aaaggatctt cacctagatc cttttaaatt aaaaatgaag     1620
ttttaaatca atctaaagta tatatgagta aacttggtct gacagttacc aatgcttaat     1680
cagtgaggca cctatctcag cgatctgtct atttcgttca tccatagttg cctgactccc     1740
cgtcgtgtag ataactacga tacgggaggg cttaccatct ggccccagtg ctgcaatgat     1800
accgcgagac ccacgctcac cggctccaga tttatcagca ataaaccagc cagccggaag     1860
ggccgagcgc agaagtggtc ctgcaacttt atccgcctcc atccagtcta ttaattgttg     1920
ccgggaagct agagtaagta gttcgccagt taatagtttg cgcaacgttg ttgccattgc     1980
tacaggcatc gtggtgtcac gctcgtcgtt tggtatggct tcattcagct ccggttccca     2040
acgatcaagg cgagttacat gatccccat gttgtgcaaa aaagcggtta gctccttcgg     2100
tcctccgatc gttgtcagaa gtaagttggc cgcagtgtta tcactcatgg ttatggcagc     2160
actgcataat tctcttactg tcatgccatc cgtaagatgc ttttctgtga ctggtgagta     2220
ctcaaccaag tcattctgag aatagtgtat gcggcgaccg agttgctctt gcccggcgtc     2280
aatacgggat aataccgcgc cacatagcag aactttaaaa gtgctcatca ttggaaaacg     2340
ttcttcgggg cgaaaactct caaggatctt accgctgttg agatccagtt cgatgtaacc     2400
cactcgtgca cccaactgat cttcagcatc ttttactttc accagcgttt ctgggtgagc     2460
aaaaacagga aggcaaaatg ccgcaaaaaa gggaataagg gcgacacgga aatgttgaat     2520
actcatactc ttccttttc aatattattg aagcatttat cagggttatt gtctcatgag     2580
cggatacata tttgaatgta tttagaaaaa taaacaaata ggggttccgc gcacatttcc     2640
ccgaaaagtg ccac                                                        2654
```

<210> SEQ ID NO 20
<211> LENGTH: 2712
<212> TYPE: DNA
<213> ORGANISM: artificial sequence
<220> FEATURE:
<223> OTHER INFORMATION: plasmid vector

<400> SEQUENCE: 20

```
ctaaattgta agcgttaata ttttgttaaa attcgcgtta aattttttgtt aaatcagctc      60 attttttaac caataggccg aaatcggcaa aatcccttat aaatcaaaag aatagaccga     120
gatagggttg agtgttgttc cagtttggaa caagagtcca ctattaaaga acgtggactc     180
```

-continued

| | |
|---|---|
| caacgtcaaa gggcgaaaaa ccgtctatca gggcgatggc ccactacgtg aaccatcacc | 240 |
| ctaatcaagt tttttggggt cgaggtgccg taaagcacta atcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtaatgcg gccgctacat gaattcaatt gttatccgct | 540 |
| cacaattcca cacaacatac gagccgggag cataaagtgt aaagcctggg gtgcctaatg | 600 |
| agtgagctaa ctcacattaa ttgcgttgcg ctcactgccc gctttccagt cgggaaacct | 660 |
| gtcgtgccag ctgcattaat gaatcggcca acgcgcgggg agaggcggtt tgcgtattgg | 720 |
| gcgctcttcc gctaggtggg ctgcaaaaca aaacggcctc ctgtcaggaa gccgctttta | 780 |
| tcgggtacgc ttcctcgctc actgactcgc tgcgctcggt cgttcggctg cggcgagcgg | 840 |
| tatcagctca ctcaaaggcg gtaatacggt tatccacaga atcaggggat aacgcaggaa | 900 |
| agaacatgtg agcaaaaggc cagcaaaagg ccaggaaccg taaaaaggcc gcgttgctgg | 960 |
| cgttttttcca taggctccgc ccccctgacg agcatcacaa aaatcgacgc tcaagtcaga | 1020 |
| ggtggcgaaa cccgacagga ctataaagat accaggcgtt tcccctgga agctccctcg | 1080 |
| tgcgctctcc tgttccgacc ctgccgctta ccggatacct gtccgccttt ctcccttcgg | 1140 |
| gaagcgtggc gctttctcat agctcacgct gtaggtatct cagttcggtg taggtcgttc | 1200 |
| gctccaagct gggctgtgtg cacgaacccc ccgttcagcc cgaccgctgc gccttatccg | 1260 |
| gtaactatcg tcttgagtcc aacccggtaa gacacgactt atcgccactg gcagcagcca | 1320 |
| ctggtaacag gattagcaga gcgaggtatg taggcggtgc tacagagttc ttgaagtggt | 1380 |
| ggcctaacta cggctacact agaaggacag tatttggtat ctgcgctctg ctgaagccag | 1440 |
| ttaccttcgg aaaaagagtt ggtagctctt gatccggcaa acaaaccacc gctggtagcg | 1500 |
| gtggtttttt tgtttgcaag cagcagatta cgcgcagaaa aaaaggatct caagaagatc | 1560 |
| ctttgatctt ttctacgggg tctgacgctc agtggaacga aaactcacgt taagggattt | 1620 |
| tggtcatgag attatcaaaa aggatcttca cctagatcct tttaaattaa aaatgaagtt | 1680 |
| ttaaatcaat ctaaagtata tatgagtaaa cttggtctga cagttaccaa tgcttaatca | 1740 |
| gtgaggcacc tatctcagcg atctgtctat ttcgttcatc catagttgcc tgactccccg | 1800 |
| tcgtgtagat aactacgata cgggagggct taccatctgg ccccagtgct gcaatgatac | 1860 |
| cgcgagaccc acgctcaccg gctccagatt tatcagcaat aaaccagcca gccggaaggg | 1920 |
| ccgagcgcag aagtggtcct gcaactttat ccgcctccat ccagtctatt aattgttgcc | 1980 |
| gggaagctag agtaagtagt tcgccagtta atagtttgcg caacgttgtt gccattgcta | 2040 |
| caggcatcgt ggtgtcacgc tcgtcgtttg gtatggcttc attcagctcc ggttcccaac | 2100 |
| gatcaaggcg agttacatga tcccccatgt tgtgcaaaaa agcggttagc tccttcggtc | 2160 |
| ctccgatcgt tgtcagaagt aagttggccg cagtgttatc actcatggtt atggcagcac | 2220 |
| tgcataattc tcttactgtc atgccatccg taagatgctt ttctgtgact ggtgagtact | 2280 |
| caaccaagtc attctgagaa tagtgtatgc ggcgaccgag ttgctcttgc ccggcgtcaa | 2340 |
| tacgggataa taccgcgcca catagcagaa ctttaaaagt gctcatcatt ggaaaacgtt | 2400 |
| cttcggggcg aaaactctca aggatcttac cgctgttgag atccagttcg atgtaaccca | 2460 |
| ctcgtgcacc caactgatct tcagcatctt ttactttcac cagcgtttct gggtgagcaa | 2520 |
| aaacaggaag gcaaaatgcc gcaaaaaagg gaataagggc gacacggaaa tgttgaatac | 2580 |

```
tcatactctt ccttttcaa tattattgaa gcatttatca gggttattgt ctcatgagcg    2640
gatacatatt tgaatgtatt tagaaaaata aacaaatagg ggttccgcgc acatttcccc    2700
gaaaagtgcc ac                                                        2712

<210> SEQ ID NO 21
<211> LENGTH: 2750
<212> TYPE: DNA
<213> ORGANISM: artificial sequence
<220> FEATURE:
<223> OTHER INFORMATION: plasmid vector

<400> SEQUENCE: 21
gtggcacttt tcggggaaat gtgcgcggaa cccctatttg tttattttc taaatacatt     60 caaatatgta tccgctcatg agacaataac cctgataaat gcttcaataa tattgaaaaa    120
ggaagagtat gagtattcaa catttccgtg tcgcccttat ccctttttt gcggcatttt    180 gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcacttttaa agttctgcta tgtggcgcgg    360
tattatcccg tattgacgcc gggcaagagc aactcggtcg ccgcatacac tattctcaga    420
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg cttttttgca caacatgggg gatcatgtaa    600
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt    1020
agattgattt aaaacttcat ttttaattta aaaggatcta ggtgaagatc cttttttgata    1080 atctcatgac caaaatccct taacgtgagt tttcgttcca ctgagcgtca gaccccgtag    1140
aaaagatcaa aggatcttct tgagatcctt tttttctgcg cgtaatctgc tgcttgcaaa    1200
caaaaaaacc accgctacca gcggtggttt gtttgccgga tcaagagcta ccaactcttt    1260
ttccgaaggt aactggcttc agcagagcgc agataccaaa tactgtcctt ctagtgtagc    1320
cgtagttagg ccaccacttc aagaactctg tagcaccgcc tacatacctc gctctgctaa    1380
tcctgttacc agtggctgct gccagtggcg ataagtcgtg tcttaccggg ttggactcaa    1440
gacgatagtt accggataag gcgcagcggt cgggctgaac ggggggttcg tgcacacagc    1500
ccagcttgga gcgaacgacc tacaccgaac tgagatacct acagcgtgag ctatgagaaa    1560
gcgccacgct tcccgaaggg agaaaggcgg acaggtatcc ggtaagcggc agggtcggaa    1620
caggagagcg cacgagggag cttccagggg gaaacgcctg gtatctttat agtcctgtcg    1680
ggtttcgcca cctctgactt gagcgtcgat ttttgtgatg ctcgtcaggg gggcggagcc    1740
tatggaaaaa cgccagcaac gcggcctttt tacggttcct ggccttttgc tggccttttg    1800
ctcacatgtt ctttcctgcg ttatcccctg attctgtgga taaccgtatt accgcctttg    1860
```

```
agtgagctga taccgctcgc cgcagccgaa cgaccgagcg cagcgagtca gtgagcgagg    1920
aagcgtaccc gataaaagcg gcttcctgac aggaggccgt tttgttttgc agcccaccta    1980
gcggaagagc gcccaatacg caaaccgcct ctccccgcgc gttggccgat tcattaatgc    2040
agctggcacg acaggtttcc cgactggaaa gcgggcagtg agcgcaacgc aattaatgtg    2100
agttagctca ctcattaggc accccaggct ttacactttta tgctcccggc tcgtatgttg    2160
tgtggaattg tgagcggata acaattgaat tcacatctag atatctcgag tcaatactag    2220
tggccaggcc ggccagcggc cgcattaccg atcgcccttc ccaacagttg cgcagcctga    2280
atggcgaatg gacgcgccc tgtagcggcg cattaagcgc ggcgggtgtg gtggttacgc      2340
gcagcgtgac cgctacactt gccagcgccc tagcgcccgc tcctttcgct ttcttccctt    2400
cctttctcgc cacgttcgcc ggctttcccc gtcaagctct aaatcggggg ctcccttttag   2460 ggttccgatt tagtgcttta cggcacctcg accccaaaaa acttgattag ggtgatggtt    2520
cacgtagtgg gccatcgccc tgatagacgg ttttttcgcc tttgacgttg gagtccacgt    2580
tctttaatag tggactcttg ttccaaactg gaacaacact caaccctatc tcggtctatt    2640
cttttgattt ataagggatt ttgccgattt cggcctattg gttaaaaaat gagctgattt    2700
aacaaaaatt taacgcgaat tttaacaaaa tattaacgct tacaatttag              2750

<210> SEQ ID NO 22
<211> LENGTH: 102
<212> TYPE: DNA
<213> ORGANISM: artificial sequence
<220> FEATURE:
<223> OTHER INFORMATION: oligonucleotide

<400> SEQUENCE: 22
aattcaagga gttaattatg aaaaaaaccg cgattgcgat tgcggtggcg ctggcgggct       60
ttgcgaccgt ggcccaggcg gcctctagaa tctgcggccg ca                         102

<210> SEQ ID NO 23
<211> LENGTH: 102
<212> TYPE: DNA
<213> ORGANISM: artificial sequence
<220> FEATURE:
<223> OTHER INFORMATION: oligonucleotide

<400> SEQUENCE: 23
ctagtgcggc cgcagattct agaggccgcc tgggccacgg tcgcaaagcc cgccagcgcc       60
accgcaatcg caatcgcggt ttttttcata attaactcct tg                          102

<210> SEQ ID NO 24
<211> LENGTH: 565
<212> TYPE: DNA
<213> ORGANISM: artificial sequence
<220> FEATURE:
<223> OTHER INFORMATION: stuffer sequence

<400> SEQUENCE: 24
tctagataac tgtggctgca ccatctgtct tcatcttccc gccatctgat gagcagttga       60
aatctggaac tgcctctgtt gtgtgcctgc tgaataactt ctatcccaga gaggccaaag      120
tacagtggaa ggtggataac gccctccaat cgggtaactc ccaggagagt gtcacagagc      180
aggacagcaa ggacagcacc tacagcctca gcagcaccct gacgctgagc aaagcagact      240
acgagaaaca caaagtctac gcctgcgaag tcacccatca gggcctgagc tccgaggtg      300 cctcagtcgt gtgcttcttg aacaacttct accccaaaga catcaatgtc aagtggaaga      360
```

```
ttgatggcag tgaacgacaa aatggcgtcc tgaacagttg gactgatcag gacagcaaag      420
acagcaccta cagcatgagc agcaccctca cgttgaccaa ggacgagtat gaacgacata      480
acagctatac ctgtgaggcc actcacaaga catcaacttc acccattgtc aagagcttca      540
acaggaatga gtgttaagcg gccgc                                            565

<210> SEQ ID NO 25
<211> LENGTH: 1131
<212> TYPE: DNA
<213> ORGANISM: artificial sequence
<220> FEATURE:
<223> OTHER INFORMATION: stuffer sequence

<400> SEQUENCE: 25
ctcgagctga tgagccatgg aagctgtgtc gcctgcacca ggctcccacg gctcgtggtg       60
cggtgcgctt ctggtgttcg ctgcctacag ccgacacgtc gagcttcgtg cccctagagt      120
tgcgcgtcac agcagcctcc ggcgctccgc gatatcaccg tgtcatccac atcaatgaag      180
tagtgctcct agacgccccc gtggggctgg tggcgcggtt ggctgacgag agcggccacg      240
tagtgttgcg ctggctcccg ccgcctgaga cacccatgac gtctcacatc cgctacgagg      300
tggacgtctc ggccggcaac ggcgcaggga gcgtacagag ggtggagatc ctggagggcc      360
gcaccgagtg tgtgctgagc aacctgcggg gccggacgcg ctacaccttc gccgtccgcg      420
cgcgtatggc tgagccgagc ttcggcggct tctggagcgc ctggtcggag cctgtgtcgc      480
tgctgacgcc tagcgacctg gaccccctca tcctgacgct ctccctcatc ctcgtggtca      540
tcctggtgct gctgaccgtg ctcgcgctgc tctcccaccg ccgggctctg aagcagaaga      600
tctggcctgg catcccgagc ccagagagcg agtttgaagg cctcttcacc acccacaagg      660
gtaacttcca gctgtggctg taccagaatg atggctgcct gtggtggagc ccctgcaccc      720
ccttcacgga ggacccacct gcttccctgg aagtcctctc agagcgctgc tgggggacga      780
tgcaggcagt ggagccgggg acagatgatg agggccctt tccccctcgt ctcctgtgag      840
aattccccgt cggatacgag cagcgtggcc gttggctgcc tcgcacagga cttccttccc      900
gactccatca ctttctcctg gaaatacaag aacaactctg acatcagcag cacccggggc      960
ttcccatcag tcctgagagg gggcaagtac gcagccacct cacaggtgct gctgccttcc     1020
aaggacgtca tgcagggcac agacgaacac gtggtgtgca aagtccagca ccccaacggc     1080
aacaaagaaa agaacgtgcc tcttccagtg attgctgagc tgcctactag t              1131

<210> SEQ ID NO 26
<211> LENGTH: 1121
<212> TYPE: DNA
<213> ORGANISM: artificial sequence
<220> FEATURE:
<223> OTHER INFORMATION: stuffer sequence

<400> SEQUENCE: 26
ctcgagctga tgagccatgg aagctgtgtc gcctgcacca ggctcccacg gctcgtggtg       60
cggtgcgctt ctggtgttcg ctgcctacag ccgacacgtc gagcttcgtg cccctagagt      120
tgcgcgtcac agcagcctcc ggcgctccgc gatatcaccg tgtcatccac atcaatgaag      180
tagtgctcct agacgccccc gtggggctgg tggcgcggtt ggctgacgag agcggccacg      240
tagtgttgcg ctggctcccg ccgcctgaga cacccatgac gtctcacatc cgctacgagg      300
tggacgtctc ggccggcaac ggcgcaggga gcgtacagag ggtggagatc ctggagggcc      360
```

-continued

```
gcaccgagtg tgtgctgagc aacctgcggg gccggacgcg ctacaccttc gccgtccgcg      420
cgcgtatggc tgagccgagc ttcggcggct tctggagcgc ctggtcggag cctgtgtcgc      480
tgctgacgcc tagcgacctg gaccccctca tcctgacgct ctccctcatc ctcgtggtca      540
tcctggtgct gctgaccgtg ctcgcgctgc tctcccaccg ccgggctctg aagcagaaga      600
tctggcctgg catcccgagc ccagagagcg agtttgaagg cctcttcacc acccacaagg      660
gtaacttcca gctgtggctg taccagaatg atggctgcct gtggtggagc ccctgcaccc      720
ccttcacgga ggacccacct gcttccctgg aagtcctctc agagcgctgc tggggacga       780 tgcaggcagt ggagccgggg acagatgatg agggcccatc ggtcttcccc ctggcaccct      840
cctccaagag cacctctggc ggcacagcgg ccctgggctg cctggtcaag gactacttcc      900
ccgaaccggt gacggtgtcg tggaactcag gcgctctgac cagcggcgtg cacaccttcc      960
cggctgtcct acagtcctca ggactctact ccctcagcag cgtggtgacc gtgccatcca     1020
gcagcttggg cacccagacc tacatctgca acgtgaatca caagcccagc aacaccaagg     1080
tggacaagaa agttgagccc aaatcttgtg acaaaactag t                         1121
```

<210> SEQ ID NO 27
<211> LENGTH: 337
<212> TYPE: DNA
<213> ORGANISM: artificial sequence
<220> FEATURE:
<223> OTHER INFORMATION: stuffer sequence

<400> SEQUENCE: 27

```
tctagataac tgtggctgca ccatctgtct tcatcttccc gccatctgat gagcagttga       60
aatctggaac tgcctctgtt gtgtgcctgc tgaataactt ctatcccaga gaggccaaag      120
tacagtggaa ggtggataac gccctccaat cgggtaactc ccaggagagt gtcacagagc      180
aggacagcaa ggacagcacc tacagcctca gcagcaccct gacgctgagc aaagcagact      240
acgagaaaca caaagtctac gcctgcgaag tcacccatca gggcctgagc tcgcccgtca      300
caaagagctt caacagggga gagtgttaag cggccgc                              337
```

<210> SEQ ID NO 28
<211> LENGTH: 509
<212> TYPE: DNA
<213> ORGANISM: artificial sequence
<220> FEATURE:
<223> OTHER INFORMATION: stuffer sequence

<400> SEQUENCE: 28

```
tctagataac tgtggctgca ccatctgtct tcatcttccc gccatctgat gagcagttga       60
aatctggaac tgcctctgtt gtgtgcctgc tgaataactt ctatcccaga gaggccaaag      120
tacagtggaa ggtggataac gccctccaat cgggtaactc ccaggagagt gtcacagagc      180
aggacagcaa ggacagcacc tacagcctca gcagcaccct gacgctgagc aaagcagact      240
acgagaaaca caaagtctac gcctgcgaag tcacccatca gggcctgagc tctgacagtg      300
gcttggaaag cagatagcag ccccgtcaag gcgggagtgg agaccaccac accctccaaa      360
caaagcaaca acaagtacgc ggccagcagc tatctgagcc tgacgcctga gcagtggaag      420
tcccacagaa gctacagctg ccaggtcacg catgaaggga gcaccgtgga aagacagtg      480 gccccctacag aatgttcata agcggccgc                                      509
```

<210> SEQ ID NO 29
<211> LENGTH: 1059

-continued

```
<212> TYPE: DNA
<213> ORGANISM: artificial sequence
<220> FEATURE:
<223> OTHER INFORMATION: stuffer sequence

<400> SEQUENCE: 29
ctcgagctga tgagccatgg aagctgtgtc gcctgcacca ggctcccacg gctcgtggtg      60
cggtgcgctt ctggtgttcg ctgcctacag ccgacacgtc gagcttcgtg cccctagagt     120
tgcgcgtcac agcagcctcc ggcgctccgc gatatcaccg tgtcatccac atcaatgaag     180
tagtgctcct agacgcccccc gtggggctgg tggcgcggtt ggctgacgag agcggccacg    240
tagtgttgcg ctggctcccg ccgcctgaga cacccatgac gtctcacatc cgctacgagg     300
tggacgtctc ggccggcaac ggcgcaggga gcgtacagag ggtggagatc ctggagggcc     360
gcaccgagtg tgtgctgagc aacctgcggg gccggacgcg ctacaccttc gccgtccgcg     420
cgcgtatggc tgagccgagc ttcggcggct tctggagcgc ctggtcggag cctgtgtcgc     480
tgctgacgcc tagcgacctg gaccccctca tcctgacgct ctccctcatc ctcgtggtca     540
tcctggtgct gctgaccgtg ctcgcgctgc tctcccaccg ccgggctctg aagcagaaga     600
tctggcctgg catcccgagc ccagagagcg agtttgaagg cctcttcacc acccacaagg     660
gtaacttcca gctgtggctg taccagaatg atggctgcct gtggtggagc ccctgcaccc     720
ccttcacgga ggacccacct gcttccctgg aagtcctctc agagcgctgc tgggggacga     780
tgcaggcagt gggagccgggg acagatgatg agggccctag gatgcctggt caagggttat     840
ttccctgagc cagtgaccttt gacctggaac tctggatccc tgtccagtgg tgtgcacacc     900
ttcccagctg tcctgcagtc tgacctctac accctcagca gctcagtgac tgtaacctcc     960
agcacctggc ccagccagtc catcacctgc aatgtggccc acccggcaag cagcaccaag    1020
gtggacaaga aaattgagcc cagagtgccc acaactagt                           1059

<210> SEQ ID NO 30
<211> LENGTH: 1056
<212> TYPE: DNA
<213> ORGANISM: artificial sequence
<220> FEATURE:
<223> OTHER INFORMATION: stuffer sequence

<400> SEQUENCE: 30
ctcgagctga tgagccatgg aagctgtgtc gcctgcacca ggctcccacg gctcgtggtg      60
cggtgcgctt ctggtgttcg ctgcctacag ccgacacgtc gagcttcgtg cccctagagt     120
tgcgcgtcac agcagcctcc ggcgctccgc gatatcaccg tgtcatccac atcaatgaag     180
tagtgctcct agacgcccccc gtggggctgg tggcgcggtt ggctgacgag agcggccacg    240
tagtgttgcg ctggctcccg ccgcctgaga cacccatgac gtctcacatc cgctacgagg     300
tggacgtctc ggccggcaac ggcgcaggga gcgtacagag ggtggagatc ctggagggcc     360
gcaccgagtg tgtgctgagc aacctgcggg gccggacgcg ctacaccttc gccgtccgcg     420
cgcgtatggc tgagccgagc ttcggcggct tctggagcgc ctggtcggag cctgtgtcgc     480
tgctgacgcc tagcgacctg gaccccctca tcctgacgct ctccctcatc ctcgtggtca     540
tcctggtgct gctgaccgtg ctcgcgctgc tctcccaccg ccgggctctg aagcagaaga     600
tctggcctgg catcccgagc ccagagagcg agtttgaagg cctcttcacc acccacaagg     660
gtaacttcca gctgtggctg taccagaatg atggctgcct gtggtggagc ccctgcaccc     720
ccttcacgga ggacccacct gcttccctgg aagtcctctc agagcgctgc tgggggacga     780
```

| | |
|---|---|
| tgcaggcagt ggagccgggg acagatgatg agggccctag gatgcctggt caagggctat | 840 |
| ttccctgagc cagtgacagt gacctggaac tctggatccc tgtccagcgg tgtgcacacc | 900 |
| ttcccagctg tcctgcagtc tgacctctac actctgagca gctcagtgac tgtccccctcc | 960 |
| agcacctggc ccagcgagac cgtcacctgc aacgttgccc acccggccag cagcaccaag | 1020 |
| gtggacaaga aaattgtgcc cagggattgt actagt | 1056 |

<210> SEQ ID NO 31
<211> LENGTH: 4153
<212> TYPE: DNA
<213> ORGANISM: artificial sequence
<220> FEATURE:
<223> OTHER INFORMATION: plasmid vector

<400> SEQUENCE: 31

| | |
|---|---|
| gtggcacttt tcggggaaat gtgcgcggaa cccctatttg tttattttc taaatacatt | 60 |
| caaatatgta tccgctcatg agacaataac cctgataaat gcttcaataa tattgaaaaa | 120 |
| ggaagagtat gagtattcaa catttccgtg tcgcccttat tccctttttt gcggcatttt | 180 |
| gccttcctgt ttttgctcac ccagaaacgc tggtgaaagt aaaagatgct gaagatcagt | 240 |
| tgggtgcacg agtgggttac atcgaactgg atctcaacag cggtaagatc cttgagagtt | 300 |
| ttcgccccga agaacgtttt ccaatgatga gcacttttaa agttctgcta tgtggcgcgg | 360 |
| tattatcccg tattgacgcc gggcaagagc aactcggtcg ccgcatacac tattctcaga | 420 |
| atgacttggt tgagtactca ccagtcacag aaaagcatct tacggatggc atgacagtaa | 480 |
| gagaattatg cagtgctgcc ataaccatga gtgataacac tgcggccaac ttacttctga | 540 |
| caacgatcgg aggaccgaag gagctaaccg cttttttgca acatggggg atcatgtaa | 600 |
| ctcgccttga tcgttgggaa ccggagctga atgaagccat accaaacgac gagcgtgaca | 660 |
| ccacgatgcc tgtagcaatg gcaacaacgt tgcgcaaact attaactggc gaactactta | 720 |
| ctctagcttc ccggcaacaa ttaatagact ggatggaggc ggataaagtt gcaggaccac | 780 |
| ttctgcgctc ggcccttccg gctggctggt ttattgctga taaatctgga gccggtgagc | 840 |
| gtgggtctcg cggtatcatt gcagcactgg ggccagatgg taagccctcc cgtatcgtag | 900 |
| ttatctacac gacggggagt caggcaacta tggatgaacg aaatagacag atcgctgaga | 960 |
| taggtgcctc actgattaag cattggtaac tgtcagacca agtttactca tatatacttt | 1020 |
| agattgattt aaaacttcat ttttaattta aaaggatcta ggtgaagatc ctttttgata | 1080 |
| atctcatgac caaaatccct taacgtgagt tttcgttcca ctgagcgtca gaccccgtag | 1140 |
| aaaagatcaa aggatcttct tgagatcctt ttttctgcg cgtaatctgc tgcttgcaaa | 1200 |
| caaaaaaacc accgctacca gcggtggttt gtttgccgga tcaagagcta ccaactcttt | 1260 |
| ttccgaaggt aactggcttc agcagagcgc agataccaaa tactgtcctt ctagtgtagc | 1320 |
| cgtagttagg ccaccacttc aagaactctg tagcaccgcc tacatacctc gctctgctaa | 1380 |
| tcctgttacc agtggctgct gccagtggcg ataagtcgtg tcttaccggg ttggactcaa | 1440 |
| gacgatagtt accggataag cgcagcggt cgggctgaac ggggggttcg tgcacacagc | 1500 |
| ccagcttgga gcgaacgacc tacaccgaac tgagatacct acagcgtgag ctatgagaaa | 1560 |
| gcgccacgct tcccgaaggg agaaaggcgg acaggtatcc ggtaagcggc agggtcggaa | 1620 |
| caggagagcg cacgagggag cttccagggg gaaacgcctg gtatctttat agtcctgtcg | 1680 |
| ggtttcgcca cctctgactt gagcgtcgat ttttgtgatg ctcgtcaggg gggcggagcc | 1740 |
| tatggaaaaa cgccagcaac gcggcctttt tacggttcct ggccttttgc tggccttttg | 1800 |

-continued

```
ctcacatgtt ctttcctgcg ttatcccctg attctgtgga taaccgtatt accgcctttg    1860
agtgagctga taccgctcgc cgcagccgaa cgaccgagcg cagcgagtca gtgagcgagg    1920
aagcgtaccc gataaaagcg gcttcctgac aggaggccgt tttgttttgc agcccaccta    1980
gcggaagagc gcccaatacg caaaccgcct ctccccgcgc gttggccgat tcattaatgc    2040
agctggcacg acaggtttcc cgactggaaa gcgggcagtg agcgcaacgc aattaatgtg    2100
agttagctca ctcattaggc accccaggct ttacacttta tgctcccggc tcgtatgttg    2160
tgtggaattg tgagcggata caattgaat tcaaggagtt aattatgaaa aaaccgcga     2220 ttgcgattgc ggtggcgctg gcgggctttg cgaccgtggc ccaggcggcc tctagaatct    2280
gcggccgcac tagatataat taaggagata aatatgaaat atctgctgcc gaccgcggcg    2340
gcgggcctgc tgctgctggc ggcgcagccg gcgatggcgc tcgagtcaat actagtggcc    2400
aggccggcct tgaaactgtt gaaagttgtt tagcaaaacc ccatacagaa aattcattta    2460
ctaacgtctg gaaagacgac aaaactttag atcgttacgc taactatgag ggctgtctgt    2520
ggaatgctac aggcgttgta gtttgtactg gtgacgaaac tcagtgttac ggtacatggg    2580
ttcctattgg gcttgctatc cctgaaaatg agggtggtgg ctctgagggt ggcggttctg    2640
agggtggcgg ctctgagggt ggcggtacta aacctcctga gtacggtgat acacctattc    2700
cgggctatac ttatatcaac cctctcgacg gcacttatcc gcctggtact gagcaaaacc    2760
ccgctaatcc taatccttct cttgaggagt ctcagcctct taatactttc atgtttcaga    2820
ataataggtt ccgaaatagg caggggggcat taactgttta tacgggcact gttactcaag    2880
gcactgaccc cgttaaaact tattaccagt acactcctgt atcatcaaaa gccatgtatg    2940
acgcttactg gaacggtaaa ttcagagact gcgctttcca ttctggcttt aatgaggatc    3000
cattcgtttg tgaatatcaa ggccaatcgt ctgacctgcc tcaacctcct gttaatgctg    3060
gcggcggctc tggtggtggt tctggtggcg gctctgaggg tggtggctct gagggtggcg    3120
gttctgaggg tggcggctct gagggtggcg gttccggtgg tggctctggt tccggtgatt    3180
ttgattatga aaagatggca aacgctaata agggggctat gaccgaaaat gccgatgaaa    3240
acgcgctaca gtctgacgct aaaggcaaac ttgattctgt cgctactgat tacggtgctg    3300
ctatcgacgg tttcattggt gacgtttccg gccttgctaa tggtaatggt gctactggtg    3360
attttgctgg ctctaattcc caaatggctc aagtcggtga cggtgataat tcacctttaa    3420
tgaataattt ccgtcaatat ttaccttccc tccctcaatc ggttgaatgt cgcccttttg    3480
tctttggcgc tggtaaacca tatgaatttt ctattgattg tgacaaaata aacttattcc    3540
gtggtgtctt tgcgtttctt ttatatgttg ccacctttat gtatgtattt tcgacgtttg    3600
ctaacatact gcgtaataaa gagtcttaag ctagctaagc ggccgcatta ccgatcgccc    3660
ttcccaacag ttgcgcagcc tgaatggcga atgggacgcg ccctgtagcg cgcattaag    3720 cgcggcgggt gtggtggtta cgcgcagcgt gaccgctaca cttgccagcg ccctagcgcc    3780
cgctcctttc gctttcttcc cttcctttct cgccacgttc gccggctttc cccgtcaagc    3840
tctaaatcgg gggctccctt tagggttccg atttagtgct ttacggcacc tcgaccccaa    3900
aaaacttgat tagggtgatg gttcacgtag tgggccatcg ccctgataga cggttttcg    3960 cccttgacg ttggagtcca cgttctttaa tagtggactc ttgttccaaa ctggaacaac    4020
```

```
actcaaccct atctcggtct attcttttga tttataaggg attttgccga tttcggccta    4080
ttggttaaaa aatgagctga tttaacaaaa atttaacgcg aattttaaca aaatattaac    4140
gcttacaatt tag                                                       4153
```